(12) United States Patent
Ohnuma et al.

(10) Patent No.: US 9,201,055 B2
(45) Date of Patent: Dec. 1, 2015

(54) STATE DETERMINING METHOD, STATE IMPARTING SYSTEM, AND STATE DETERMINING PROGRAM

(71) Applicant: NABTESCO CORPORATION, Tokyo (JP)

(72) Inventors: Yoshinori Ohnuma, Tokyo (JP); Takuya Shirata, Tokyo (JP); Yasuhito Ida, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

(21) Appl. No.: 14/408,895

(22) PCT Filed: Jun. 21, 2013

(86) PCT No.: PCT/JP2013/067069
§ 371 (c)(1),
(2) Date: Dec. 17, 2014

(87) PCT Pub. No.: WO2013/191273
PCT Pub. Date: Dec. 27, 2013

(65) Prior Publication Data
US 2015/0177219 A1    Jun. 25, 2015

(30) Foreign Application Priority Data

Jun. 22, 2012 (JP) .................................. 2012-141486

(51) Int. Cl.
*G01N 33/28* (2006.01)
*G01N 21/25* (2006.01)
(Continued)

(52) U.S. Cl.
CPC .......... *G01N 33/2888* (2013.01); *G01N 21/251* (2013.01); *G01N 21/59* (2013.01); *G01N 21/8507* (2013.01); *G01N 21/94* (2013.01); *G01J 2003/466* (2013.01); *G01N 2021/8514* (2013.01)

(58) Field of Classification Search
CPC .  G01N 33/2888; G01N 21/29; G01N 21/251; G01N 21/293; G01N 21/534
USPC .......................................................... 356/70
See application file for complete search history.

(56) References Cited

U.S. PATENT DOCUMENTS 7,612,874 B2    11/2009   Kong et al.
2008/0024761 A1    1/2008   Kong et al.
(Continued)

FOREIGN PATENT DOCUMENTS

JP    06-034541    2/1994
JP    07-020049    1/1995
(Continued)

OTHER PUBLICATIONS

International Search Report issued in International Application No. PCT/JP2013/067069, dated Aug. 20, 2013.

*Primary Examiner* — Tarifur Chowdhury
*Assistant Examiner* — Md Rahman
(74) *Attorney, Agent, or Firm* — Pillsbury Winthrop Shaw Pittman LLP

(57) ABSTRACT

In a state determination method for determining the state of degradation of lubricating oil in a speed reducer and the state of breakage of the speed reducer, white light emitted by a white LED is transmitted through the lubricating oil, causing an RGB sensor to detect the color of the light transmitted through the lubricating oil by the white LED. The brightness of the color detected by the RGB sensor is calculated. A color component maximum difference that is the difference between a maximum value and a minimum value among the R value, G value, and B value of the color detected by the RGB sensor is calculated. The states on the basis of the calculated brightness and the calculated color component maximum difference are determined.

7 Claims, 28 Drawing Sheets

(51) Int. Cl.
*G01N 21/94* (2006.01)
*G01N 21/59* (2006.01)
*G01N 21/85* (2006.01)
*G01J 3/46* (2006.01)

(56) References Cited

U.S. PATENT DOCUMENTS

2010/0157304 A1 6/2010 Takahashi et al.
2012/0086942 A1 4/2012 Honda et al.
2013/0250281 A1* 9/2013 Shirata ............................ 356/70
2013/0250303 A1* 9/2013 Shirata et al. ................. 356/436

FOREIGN PATENT DOCUMENTS

| JP | 2000-146696 | 5/2000 |
| JP | 2007-198767 | 8/2007 |
| JP | 2012-107898 | 6/2012 |
| WO | 2010/150526 A1 | 12/2010 |
| WO | 2012/074109 A1 | 6/2012 |

* cited by examiner

Fig.14

Speed reducer A

| Deterioration state of lubricating oil | No deterioration |
|---|---|
| State of speed reducer | Normal |

Speed reducer B

| Deterioration state of lubricating oil | Deterioration level high |
|---|---|
| State of speed reducer | Require overhaul and repair |

Speed reducer C

| Deterioration state of lubricating oil | Deterioration level high |
|---|---|
| State of speed reducer | Breakage |

Speed reducer D

| Deterioration state of lubricating oil | Abnormal by being mixed with impurities |
|---|---|
| State of speed reducer | — |

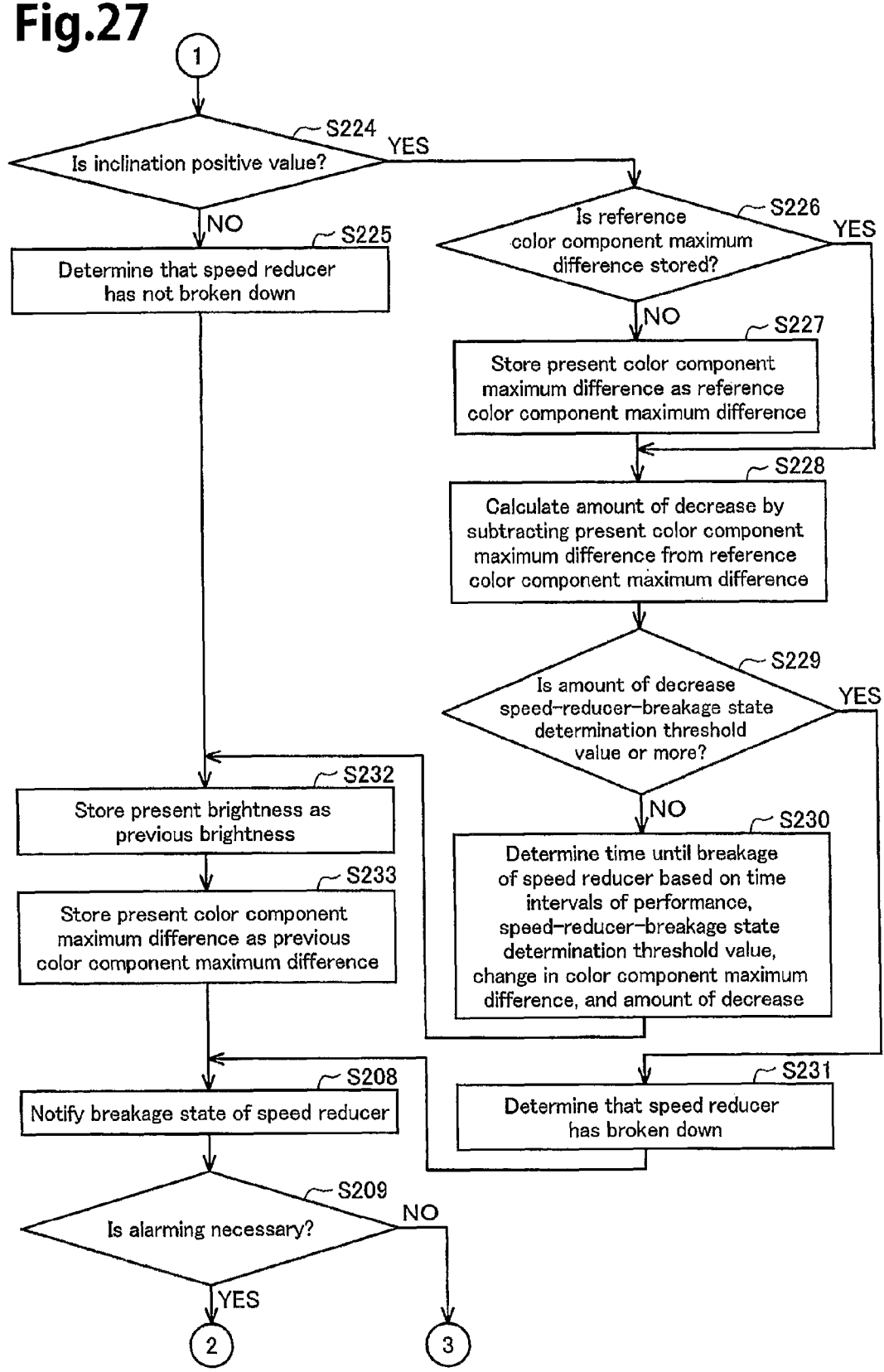

Fig.28

Speed reducer A

| Deterioration state of lubricating oil | No deterioration |
|---|---|
| State of speed reducer | Normal |

Speed reducer B

| Deterioration state of lubricating oil | Deterioration level high |
|---|---|
| State of speed reducer | 24 hours to breakage |

Speed reducer C

| Deterioration state of lubricating oil | Deterioration level high |
|---|---|
| State of speed reducer | Breakage |

Speed reducer D

| Deterioration state of lubricating oil | Abnormal by being mixed with impurities |
|---|---|
| State of speed reducer | — |

.
.
.

STATE DETERMINING METHOD, STATE IMPARTING SYSTEM, AND STATE DETERMINING PROGRAM

CROSS-REFERENCE TO RELATED APPLICATIONS

This application is the U.S. National Stage of PCT/JP2013/067069, filed Jun. 21, 2013, which in turn claims priority to Japanese Patent Application No. 2012-141486, filed Jun. 22, 2012. The contents of all of these applications are incorporated herein by reference in their entirety.

TECHNICAL FIELD OF THE INVENTION

The present invention relates to a state determining method for determining at least either one of the deterioration state of oil of a machine and the breakage state of the machine.

BACKGROUND OF THE INVENTION

A method in which white light emitted by a light-emitting element is caused to pass through oil, and a light-receiving element is caused to detect the color of light that has passed through the oil, and thereafter the deterioration state of the oil is determined based on the output of the light-receiving element has heretofore been known as a state determining method for determining the deterioration state of machine oil (see Patent Documents 1 to 3, for example).

The state determining method disclosed by Patent Document 1 is a method in which one color that is suitable for each kind of oil is selected from among red, green, and blue components of light detected by a light-receiving element, and the deterioration state of the oil is determined based on optical absorbance with respect to the selected one color.

The state determining method disclosed by Patent Document 2 is a method in which the deterioration state of oil, i.e., the kind and amount of foreign substances that mix with oil are determined based on the difference between the optical absorbance of a red component of light detected by a light-receiving element and the optical absorbance of a blue component thereof.

The state determining method disclosed by Patent Document 3 is a method in which the state of chemical deterioration of oil is determined based on the ratio between the value of a red component of light detected by a light-receiving element and the value of a green component thereof, and the amount of foreign substances that mix with the oil is determined based on a change in optical absorbance of each of the red, green, and blue components of light detected by the light-receiving element.

PRIOR ART DOCUMENTS

Patent Documents

Patent Document 1: Japanese Laid-Open Patent Publication No. 6-34541
Patent Document 2: Japanese Laid-Open Patent Publication No. 2007-198767
Patent Document 3: U.S. Pat. No. 7,612,874

SUMMARY OF THE INVENTION

However, the inventors of the present invention were not satisfied with the determination accuracy of the deterioration state of oil in the methods of Patent Documents 1 to 3.

Additionally, in the methods of Patent Documents 1 to 3, it is impossible to determine the breakage state of a machine.

Therefore, it is an objective of the present invention to provide a state determining method that is capable of determining at least either one of the deterioration state of oil of a machine and the breakage state of the machine with higher accuracy than conventional methods.

The state determining method of the present invention is a method for determining at least either one of a deterioration state of oil of a machine and a breakage state of the machine. The method includes: a light emission step of causing white light emitted by a light-emitting element to pass through the oil; a light receiving step of causing a light-receiving element to detect a color of the light that has passed through the oil according to the light emission step; a brightness calculation step of calculating brightness of the color detected according to the light receiving step; a color component calculation value calculating step of calculating a color component calculation value that is a value calculated based on a maximum value and a minimum value among an R value, a G value, and a B value of the color detected according to the light receiving step; and a state determination step of determining the state based on the brightness calculated according to the brightness calculation step and the color component calculation value calculated according to the color component calculation value calculating step. The color component calculation value is one of a difference between the maximum value and the minimum value, a ratio between the maximum value and the minimum value, an integral value of the brightness of the difference between the maximum value and the minimum value, and an integral value of the brightness of the ratio between the maximum value and the minimum value.

The inventors of the present invention have found out through experimentation that the deterioration state of oil of a machine has a strong correlation with the brightness and the color component calculation value of the color of light detected by a light-receiving element. The inventors of the present invention also have found out through experimentation that the breakage state of the machine has a strong correlation with the brightness and the color component calculation value of the color of light detected by the light-receiving element. The state determining method of the present invention determines at least either one of the deterioration state of oil of a machine and the breakage state of the machine based on the brightness and the color component calculation value of the color of light detected by the light-receiving element, and therefore it is possible to determine at least either one of the deterioration state of the oil of the machine and the breakage state of the machine with higher accuracy than conventional methods.

In the state determining method according to the present invention, the state determination step may include an oil deterioration state determining step of determining the deterioration state of the oil. Also, the oil deterioration state determining step may be a step of determining that the deterioration state of the oil is a state predetermined with respect to a combination of the brightness calculated according to the brightness calculation step and the color component calculation value calculated according to the color component calculation value calculating step.

According to this configuration, the state determining method of the present invention determines the deterioration state of machine oil based on a combination of the brightness and the color component calculation value of the color of light detected by the light-receiving element, and therefore there is no need to perform a complicated process in order to determine the deterioration state of the machine oil. Therefore, the state determining method of the present invention is capable of lessening a burden imposed to determine the deterioration state of the machine oil.

In the state determining method according to present invention, the state determination step may include a machine breakage state determining step of determining the breakage state of the machine. The machine breakage state determining step may be a step of determining that the breakage state of the machine is a state predetermined with respect to a combination of the brightness calculated according to the brightness calculation step and the color component calculation value calculated according to the color component calculation value calculating step.

According to this configuration, the state determining method of the present invention determines the breakage state of a machine based on a combination of the brightness and the color component calculation value of the color of light detected by the light-receiving element, and therefore there is no need to perform a complicated process in order to determine the breakage state of the machine. Therefore, the state determining method of the present invention is capable of lessening a burden imposed to determine the breakage state of the machine.

In the state determining method according to present invention, the state determination step may include a machine breakage state determining step of determining the breakage state of the machine, and the color component calculation value may be a difference between the maximum value and the minimum value. The machine breakage state determining step may be a step of determining the breakage state of the machine in accordance with an amount of decrease in the color component calculation value in comparison with that at a point of time when both the brightness calculated according to the brightness calculation step and the color component calculation value calculated according to the color component calculation value calculating step start to decrease.

According to this configuration, when the color component calculation value is the difference between the maximum value and the minimum value among the R value, the G value, and the B value of the color detected according to the light receiving step, the state determining method of the present invention determines the breakage state of the machine not based on a simple combination of the brightness and the color component calculation value of the color of light detected by the light-receiving element, but based on a change in the brightness and in the color component calculation value of the color of light detected by the light-receiving element, and therefore it is possible to reduce the influence of the individual differences of the machine and the influence of the individual differences of the oil on the determination of the breakage state of the machine. Therefore, the state determining method of the present invention is capable of raising the accuracy of the determination of the breakage state of the machine.

The state determining method according to present invention may be configured that, when both the brightness calculated according to the brightness calculation step and the color component calculation value calculated according to the color component calculation value calculating step decrease, the machine breakage state determining step is a step of determining time until the machine breaks down as the breakage state of the machine in accordance with time intervals at which the machine breakage state determining step is performed and in accordance with an amount of decrease in the color component calculation value at the time intervals.

According to this configuration, the state determining method of the present invention determines time until breakdown of the machine, and therefore it is possible to improve the convenience of a user of the machine.

The state determining method according to present invention may further include a received-light output adjusting step of adjusting an output of the light-receiving element. The received-light output adjusting step is a step of turning the color of the output of the light-receiving element black when an arrival of the light at the light-receiving element is intercepted and of turning the color of the output of the light-receiving element white when the oil is introduced into the machine.

According to this configuration, the state determining method of the present invention adjusts the output of the light-receiving element for each kind of oil, and therefore it is possible to reduce the influence of the individual differences of the oil types on the determination of the state.

In the state determining method according to present invention, the color component calculation value may be a difference between the maximum value and the minimum value, and the color component calculation value calculating step may be a step of calculating a difference between the R value and the B value of the color detected according to the light receiving step as the color component calculation value.

According to this configuration, the state determining method of the present invention is not required to determine which value is the maximum and which value is the minimum among the R, G, and B values of the color detected according to the light receiving step each time, and therefore it is possible to reduce a burden imposed to calculate the color component calculation value.

The state notification system according to the present invention is a system for notifying at least either one of a deterioration state of oil of a machine and a breakage state of the machine. The system includes a light-emitting element that emits white light, a light-receiving element that detects a color of received light, a gap-forming member in which a gap for oil into which the oil enters is located on an optical path from the light-emitting element to the light-receiving element, a brightness calculating means for calculating brightness of the color detected by the light-receiving element, a color-component calculation value calculating means for calculating a color component calculation value that is a value calculated based on a maximum value and a minimum value among an R value, a G value, and a B value of the color detected by the light-receiving element, a state determining means for determining the state based on the brightness calculated by the brightness calculating means and the color component calculation value calculated by the color-component calculation value calculating means, and a display device that notifies the state determined by the state determining means. The color component calculation value is any one of a difference between the maximum value and the minimum value, a ratio between the maximum value and the minimum value, an integral value of the brightness of the difference between the maximum value and the minimum value, and an integral value of the brightness of the ratio between the maximum value and the minimum value.

According to this configuration, the state notification system of the present invention determines at least either one of the deterioration state of oil of a machine and the breakage state of the machine based on the brightness and the color component calculation value of the color of light detected by the light-receiving element, and therefore it is possible to determine at least either one of the deterioration state of the oil of the machine and the breakage state of the machine with higher accuracy than conventional methods.

The state determining program according to the present invention is a program for determining at least either one of a deterioration state of oil of a machine and a breakage state of the machine. The program causes a computer to perform: a brightness calculation step of calculating brightness of a color of light detected by a light-receiving element at which white light that has been emitted by a light-emitting element and passed through the oil and arrives; a color component calculation value calculating step of calculating a color component calculation value that is a value calculated based on a maximum value and a minimum value among an R value, a G value, and a B value of the color detected by the light-receiving element; and a state determination step of determining the state based on the brightness calculated according to the brightness calculation step and the color component calculation value calculated according to the color component calculation value calculating step. The color component calculation value is any one of a difference between the maximum value and the minimum value, a ratio between the maximum value and the minimum value, an integral value of the brightness of the difference between the maximum value and the minimum value, and an integral value of the brightness of the ratio between the maximum value and the minimum value.

According to this configuration, the computer that performs the state determining program of the present invention determines at least either one of the deterioration state of oil of a machine and the breakage state of the machine based on the brightness and the color component calculation value of the color of light detected by the light-receiving element, and therefore it is possible to determine at least either one of the deterioration state of the oil of the machine and the breakage state of the machine with higher accuracy than conventional methods.

EFFECTS OF THE INVENTION

The state determining method of the present invention is capable of determining at least either one of the deterioration state of oil of a machine and the breakage state of the machine with higher accuracy than conventional methods.

BRIEF DESCRIPTION OF THE DRAWINGS

FIG. 14 is a diagram showing an example of the display of a display portion shown in FIG. 6;

FIG. 27 is a flowchart of an operation subsequent to the operation of FIG. 26; and FIG. 28 is a diagram showing an example of the display of a display portion shown in FIG. 24.

DETAILED DESCRIPTION OF THE PREFERRED EMBODIMENTS

Embodiments of the present invention will now be described with reference to the drawings.

First Embodiment

First, a configuration to implement a state determining method according to the present embodiment will be described.

Figure 1:
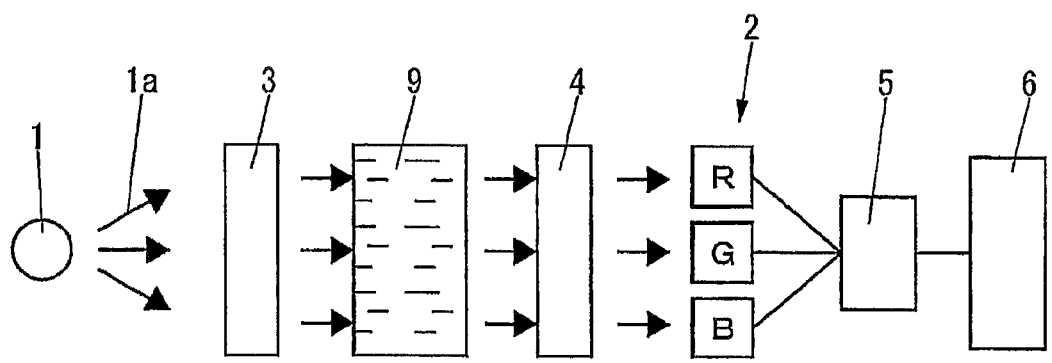
FIG. 1 is a block diagram of a configuration to implement a state determining method according to a first embodiment of the present invention.

FIG. 1 is a block diagram of a configuration to implement a state determining method according to the present embodiment.

As shown in FIG. 1, the state determining method according to the present embodiment is implemented by a light-emitting element 1 that emits white light 1a, a light-receiving element 2 that detects the color of received light 1a in an RGB format, transmission elements 3 and 4 that are arranged between the light-emitting element 1 and the light-receiving element 2 and between which oil 9 of a machine is caused to enter, an arithmetic processing portion 5 that determines the deterioration state of the oil 9 and the breakage state of a machine based on a color detected by the light-receiving element 2, and a display device 6 that displays determination results obtained by the arithmetic processing portion 5.

Figure 2:
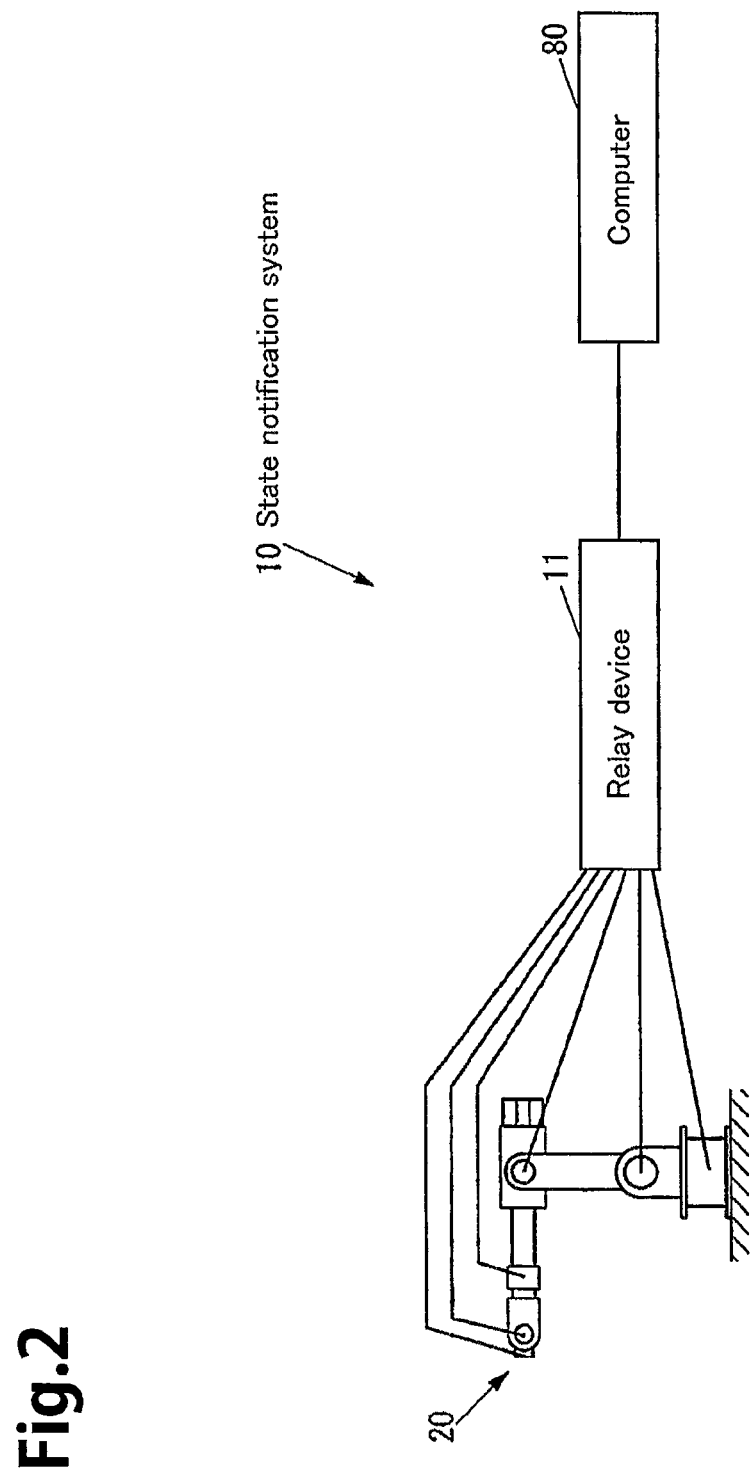
FIG. 2 is a block diagram of a state notification system that is one specific example of the configuration of FIG. 1.

FIG. 2 is a block diagram of a state notification system 10 that is one specific example of the configuration of FIG. 1.

As shown in FIG. 2, the state notification system 10 is composed of an industrial robot 20, a computer 80 such as a personal computer PC), and a relay device 11 that relays signals from a plurality of oil state sensors (described below) of the industrial robot 20 to the computer 80.

Figure 3:
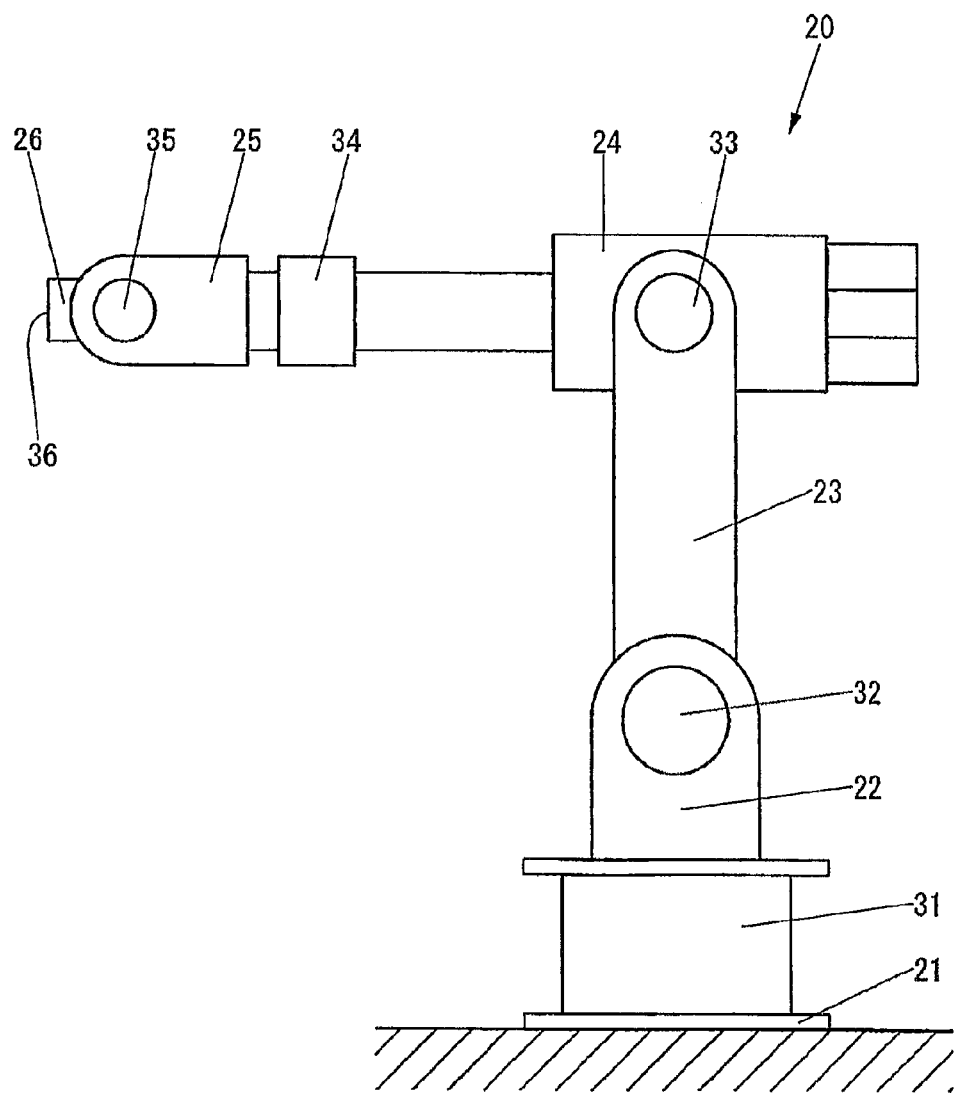
FIG. 3 is a side view of an industrial robot shown in FIG. 2.

FIG. 3 is a side view of the industrial robot 20.

As shown in FIG. 3, the industrial robot 20 is composed of an attachment portion 21 that is attached to an installation part such as a floor or a ceiling, arms 22 to 26, a joint portion 31 by which the attachment portion 21 and the arm 22 are connected together, a joint portion 32 by which the arm 22 and the arm 23 are connected together, a joint portion 33 by which the arm 23 and the arm 24 are connected together, a joint portion 34 by which the arm 24 and the arm 25 are connected together, a joint portion 35 by which the arm 25 and the arm 26 are connected together, and a joint portion 36 by which the arm 26 and a hand (not shown) are connected together.

Figure 4:
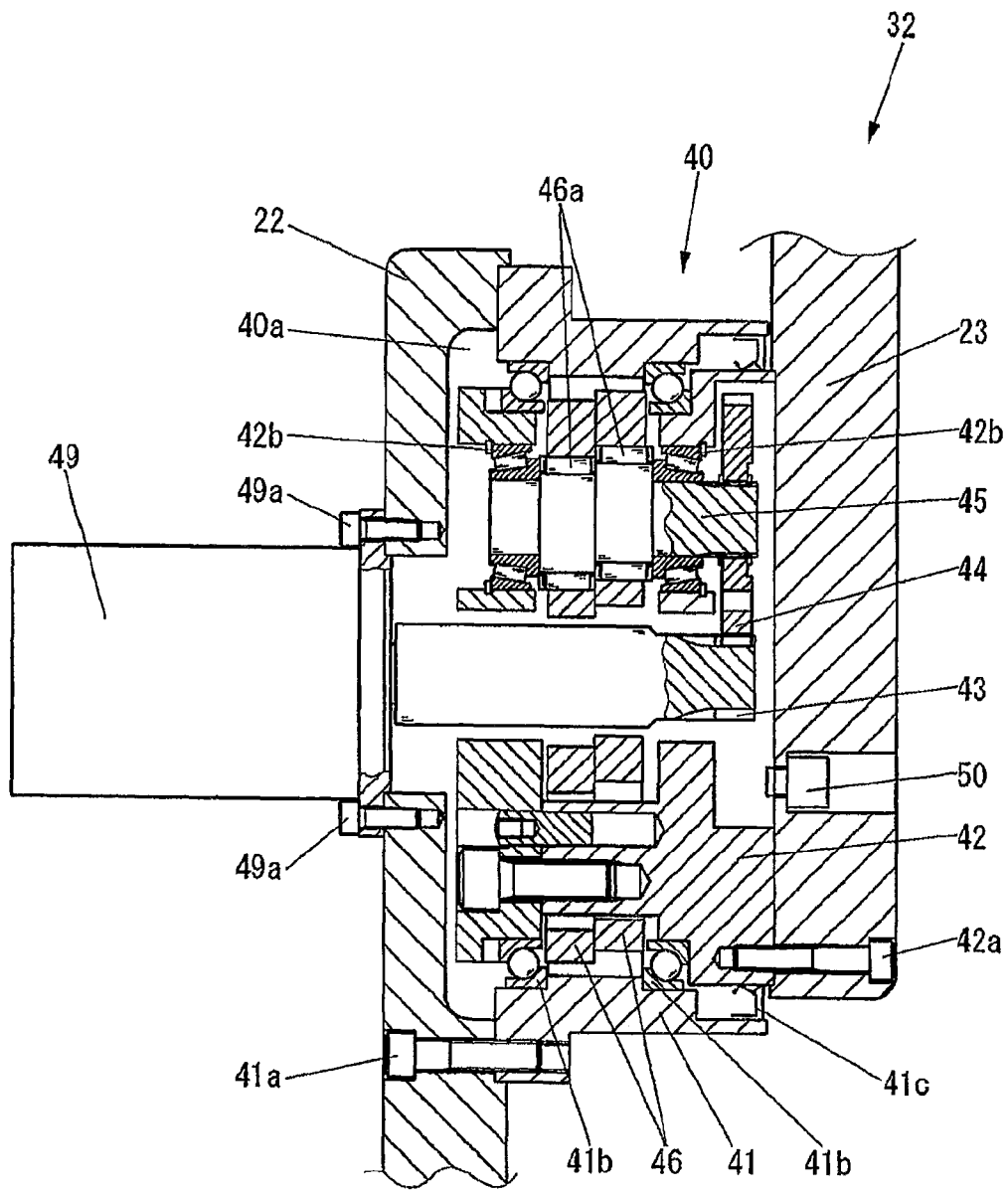
FIG. 4 is a cross-sectional view of a joint portion shown in FIG. 3.

FIG. 4 is a cross-sectional view of the joint portion 32. Although the joint portion 32 is described in the following, the same applies to the joint portions 31 and 33 to 36.

As shown in FIG. 4, the joint portion 32 is composed of a speed reducer 40 by which the arm 22 and the arm 23 are connected together, a motor 49 fixed to the arm 22 by means of bolts 49a, and an oil state sensor 50 that detects the state of lubricating oil 40a that reduces friction generated in a movable part of the speed reducer 40. The speed reducer 40 is one specific example of the machine of the present invention. The lubricating oil 40a is one specific example of the oil 9 of FIG. 1.

The speed reducer 40 is composed of a case 41 fixed to the arm 22 by means of a bolt 41a, a supporter 42 fixed to the arm 23 by means of a bolt 42a, a gear 43 fixed to an output shaft of the motor 49, three gears 44 that are evenly spaced around a central axis of the speed reducer 40 and that engage with the gear 43, three crankshafts 45 that are evenly spaced around the central axis of the speed reducer 40 and that are fixed to the gears 44, and two external gears 46 that engage with internal gears located in the case 41.

The supporter 42 is rotationally supported by the case 41 with a bearing 41b therebetween. A sealing member 41c that prevents the lubricating oil 40a from leaking out is located between the case 41 and the supporter 42.

The crankshaft 45 is rotationally supported by the supporter 42 with a bearing 42b therebetween, and is rotationally supported by the external gear 46 with a bearing 46a therebetween.

The oil state sensor 50 is fixed to the arm 23.

Figure 5:
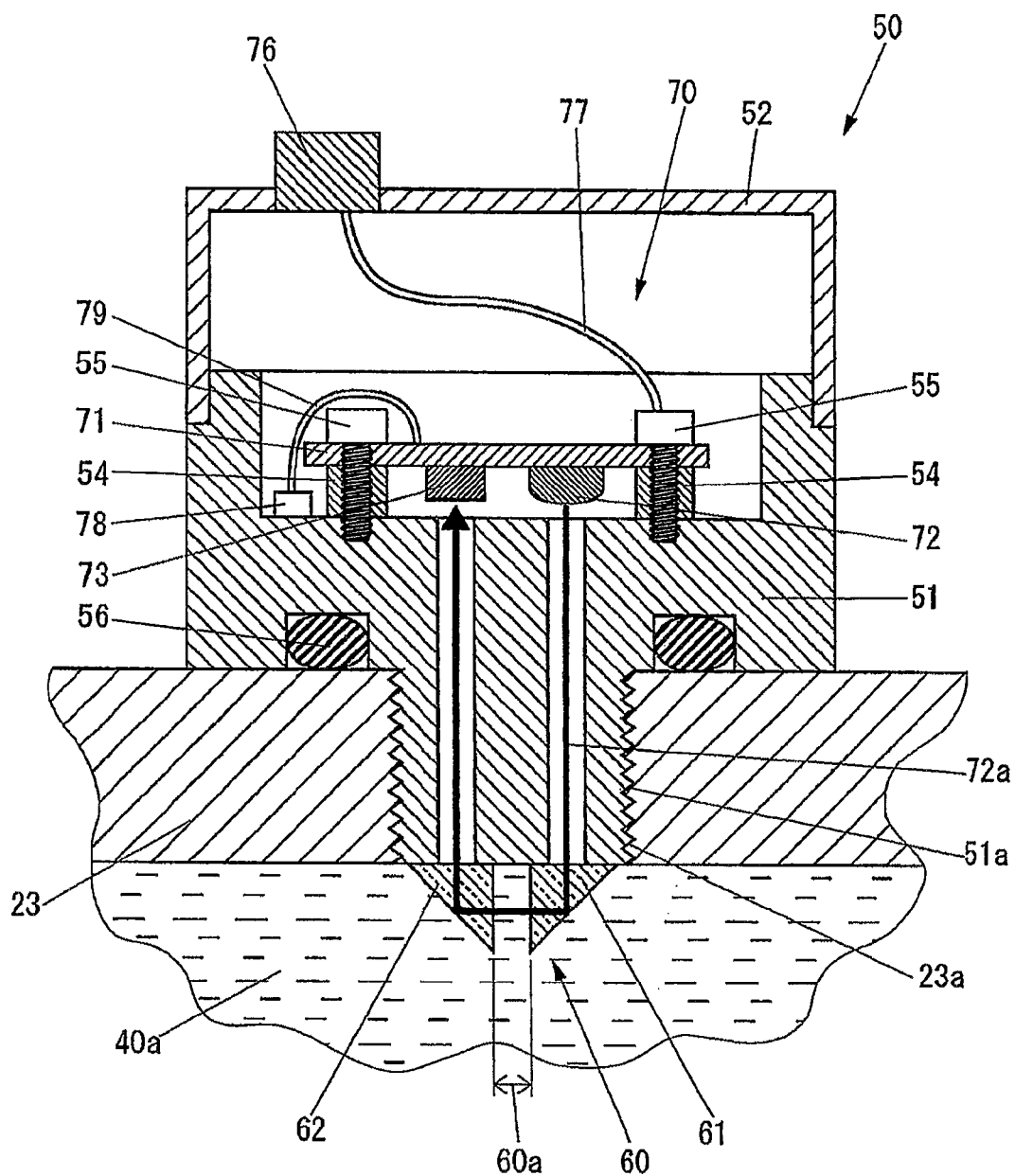
FIG. 5 is a cross-sectional front view of an oil state sensor attached to an arm shown in FIG. 4.

FIG. 5 is a cross-sectional front view of the oil state sensor 50 that has been attached to the arm 23.

As shown in FIG. 5, the oil state sensor 50 is composed of an aluminum-alloy-made housing 51 that supports each component of the oil state sensor 50, an aluminum-alloy-made cover 52 that is fixed to the housing 51, screws (not shown) by which the cover 52 is fixed to the housing 51, a spacer 54 that is arranged between the housing 51 and a circuit board 71 (described below), a hexagon socket head bolt 55 by which the circuit board 71 is fixed to the housing 51 with the spacer 54 therebetween, an O-ring 56 that prevents the lubricating oil 40a from leaking out from between the housing 51 and the arm 23, a gap-forming member 60 that is held by the housing 51, and an electronic component group 70.

The housing 51 has a threaded portion 51a that is fixed to a threaded hole 23a of the arm 23.

The gap-forming member 60 is formed of two glass-made right angle prisms 61 and 62, and an oil receiving gap 60a that is a gap into which the lubricating oil 40a enters is formed between the two right angle prisms 61 and 62. The right angle prism 61 is one specific example of the transmission element 3 of FIG. 1. The right angle prism 62 is one specific example of the transmission element 4 of FIG. 1.

The electronic component group 70 is composed of the circuit board 71 fixed to the housing 51 with the spacer 54 therebetween by means of the hexagon socket head bolt 55, a white LED (Light Emitting Diode) 72 mounted on the circuit board 71, an RGB sensor 73 mounted on the circuit board 71, a waterproof connector 76 fixed to the cover 52, a plurality of lead wires 77 by which the circuit board 71 and the waterproof connector 76 are electrically connected together, a temperature sensor 78 fixed to the housing 51, and a lead wire 79 by which the circuit board 71 and the temperature sensor 78 are electrically connected together.

A plurality of electronic components, in addition to the white LED 72 and the RGB sensor 73, are mounted on the circuit board 71.

The white LED 72 is an electronic component that emits white light, and is one specific example of the light-emitting element 1 of FIG. 1. For example, NSPW500GS-K1 manufactured by Nichia Corporation may be used as the white LED 72.

The RGB sensor 73 is an electronic component that detects the color of received light, and is one specific example of the light-receiving element 2 of FIG. 1. For example, S9032-02 manufactured by Hamamatsu Photonics K.K. may be used as the RGB sensor 73.

The waterproof connector 76 is connected to a connector of an external device of the oil state sensor 50, and is supplied with electric power from the external device through the connector of the external device, and outputs detection results of the oil state sensor 50 in the form of electric signals to the external device through the connector of the external device.

The temperature sensor 78 is an electronic component that detects the temperature of the lubricating oil 40a through the housing 51.

The oil receiving gap 60a of the gap-forming member 60 is located on an optical path 72a ranging from the white LED 72 to the RGB sensor 73.

The right angle prisms 61 and 62 transmit light emitted by the white LED 72. The right angle prism 61 has an entrance plane through which light emitted by the white LED 72 enters, a reflection plane that reflects incident light traveling from the entrance plane and bends the traveling direction of the light ninety degrees, and an emission plane from which light reflected by the reflection plane is emitted. The right angle prism 62 has an entrance plane through which light emitted from the emission plane of the right angle prism 61 enters, a reflection plane that reflects incident light traveling from the entrance plane and bends the traveling direction of the light ninety degrees, and an emission plane from which light reflected by the reflection plane is emitted.

The entrance plane, the reflection plane, and the emission plane of the right angle prism 61 and the entrance plane, the reflection plane, and the emission plane of the right angle prism 62 are optically ground. Furthermore, the reflection plane of the right angle prism 61 and the reflection plane of the right angle prism 62 are each subjected to the application of an aluminum-deposited film. Furthermore, an $MgF_2$ film or a $SiO_2$ film is applied onto the aluminum-deposited film in order to protect the aluminum-deposited film that is weak in hardness and in adhesive force.

The optical path 72a is bent ninety degrees on the reflection plane of the right angle prism 61, and is also bent ninety degrees on the reflection plane of the right angle prism 62. In other words, the optical path 72a is bent 180 degrees by means of the gap-forming member 60.

The distance between the emission plane of the right angle prism 61 and the entrance plane of the right angle prism 62, i.e., the length of the oil receiving gap 60a is, for example, 1 mm. If the length of oil receiving the gap 60a is too short, it will be difficult for contaminants contained in the lubricating oil 40a to appropriately flow through the oil receiving gap 60a, and therefore the detection accuracy of the color of the contaminants in the lubricating oil 40a will fall. On the other hand, if the length of the oil receiving gap 60a is too long, light emitted from the white LED 72 will be excessively absorbed by the contaminants contained in the lubricating oil 40a in the oil receiving gap 60a, and it will be difficult for the light to reach the RGB sensor 73, and therefore the detection accuracy of the color of the contaminants contained in the lubricating oil 40a will fall likewise. Therefore, preferably, the length of the oil receiving gap 60a is appropriately set so that the detection accuracy of the color of the contaminants contained in the lubricating oil 40a rise.

Figure 6:
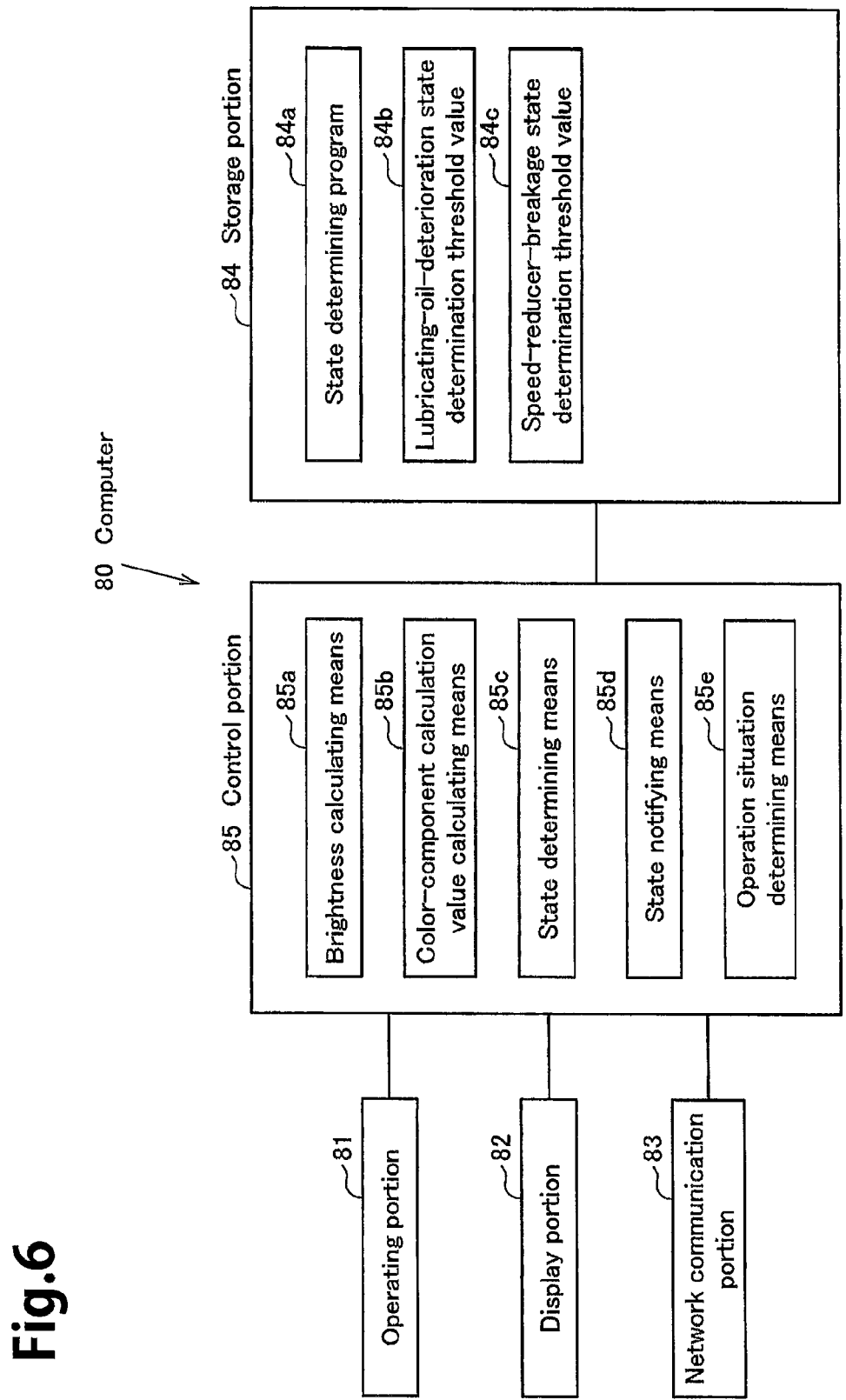
FIG. 6 is a block diagram of a computer shown in FIG. 2.

FIG. 6 is a block diagram of the computer 80.

As shown in FIG. 6, the computer 80 is composed of an operating portion 81, which is an input device, such as a mouse or a keyboard by which various operations performed by a user of the computer 80 are input, a display portion 82, which is a display device, such as a liquid crystal display (LCD), on which various pieces of information are displayed, a network communication portion 83, which is a network communication device that communicates with the relay device 11 through a network such as a LAN (Local Area Network), a storage portion 84, which is a storage device, such as an HDD (Hard Disk Drive), that stores various pieces of data, and a control portion 85, which controls the whole of the computer 80. The display portion 82 is one specific example of the display device 6 of FIG. 1. The control portion 85 is one specific example of the arithmetic processing portion 5 of FIG. 1.

The storage portion 84 stores a state determining program 84a that determines the deterioration state of the lubricating oil 40a of the speed reducer 40 of the industrial robot 20 and the breakage state of the speed reducer 40 of the industrial robot 20.

The state determining program 84a may be installed in the computer 80 in a process of manufacturing the computer 80, or may be additionally installed into the computer 80 from a storage medium such as a USB (Universal Serial Bus) memory, a compact disc (CD), or a digital versatile disc (DVD), or may be additionally installed into the computer 80 through a network.

Additionally, the storage portion 84 stores a lubricating-oil-deterioration state determination threshold value 84b, which is used to determine the deterioration state of the lubricating oil 40a, and a speed-reducer-breakage state determination threshold value 84c, which is used to determine the breakage state of the speed reducer 40.

The control portion 85 is composed of, for example, a central processing unit (CPU), a read only memory (ROM), which pre-stores a program and various pieces of data, and a random access memory (RAM), which is used as a CPU work area. The CPU executes a program stored in the ROM or in the storage portion 84.

The control portion 85 executes the state determining program 84a stored in the storage portion 84, and hence functions as a brightness calculating means 85a that calculates the brightness of a color detected by the RGB sensor 73, functions as a color-component calculation value calculating means 85b that calculates a color component calculation value that is a value calculated based on the maximum value and the minimum value among an R value, a G value, and a B value of the color detected by the RGB sensor 73, functions as a state determining means 85c that determines a state based on the brightness calculated by the brightness calculating means 85a and the color component calculation value calculated by the color-component calculation value calculating means 85b, functions as a state notifying means 85d that notifies a state determined by the state determining means 85c, and functions as an operation situation determining means 85e that determines an operation situation of the speed reducer 40.

It is possible for the brightness calculating means 85a to calculate brightness according to an expression 1 shown below by using each of the R, G, and B values of the color detected by the RGB sensor 73.

$$\sqrt{R^2+G^2+B^2} \qquad \text{[Expression 1]}$$

It is possible for the color-component calculation value calculating means 85b to calculate a color component maximum difference, which is a color component calculation value according to an expression 2 shown below by using each of the R and B values of the color detected by the RGB sensor 73. In the expression 2, MAX (R, G, B) designates the maximum value among the R, G, and B values of the color of light detected by the RGB sensor 73. MIN (R, G, B) designates the minimum value among the R, G, and B values of the color of light detected by the RGB sensor 73. In other words, the color component maximum difference is the difference between the maximum value and the minimum value among the R, G, and B values of the color detected by the RGB sensor 73.

$$MAX(R,G,B)-MIN(R,G,B) \qquad \text{[Expression 2]}$$

Next, a method for determining a lubricating-oil-deterioration state determination threshold value 84b will be described.

Figure 7:
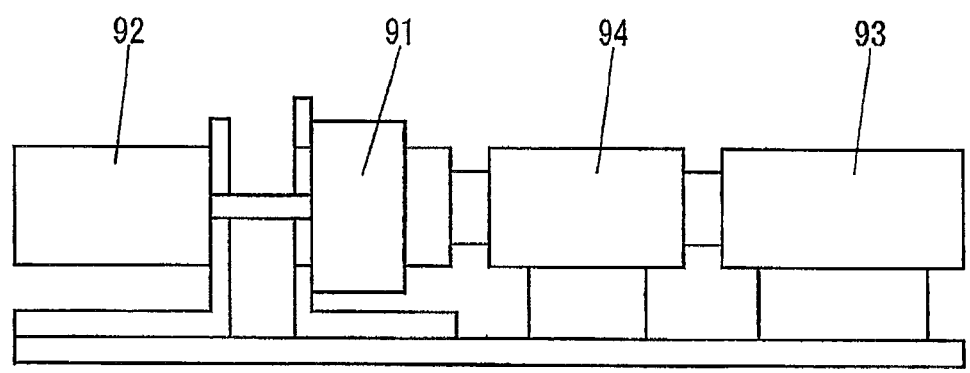
FIG. 7 is a diagram showing a configuration of an experiment performed to confirm a relationship between brightness and a color component calculation value that are calculated by the computer of FIG. 2.

FIG. 7 is a diagram showing an arrangement of an experiment to confirm the relationship between brightness and a color component calculation value calculated by the computer 80.

The configuration of FIG. 7 is composed of a speed reducer 91 that is the same in type as the speed reducer 40, a motor 92 that inputs a rotational force into the speed reducer 91, a torque adding device 93 that adds torque to the speed reducer 91, and a torque meter 94 that measures torque added to the speed reducer 91 by means of the torque adding device 93.

The speed reducer 91 has its stationary case, and has its supporter connected to the torque adding device 93 through the torque meter 94. The speed reducer 91 is provided with an oil state sensor that is the same in type as the oil state sensor 50.

The output of the RGB sensor of the oil state sensor is input to a computer that has the same configuration as the computer 80 while adding constant torque to the speed reducer 91. The output of the RGB sensor of the oil state sensor is adjusted in the same way as described below.

Figure 8:
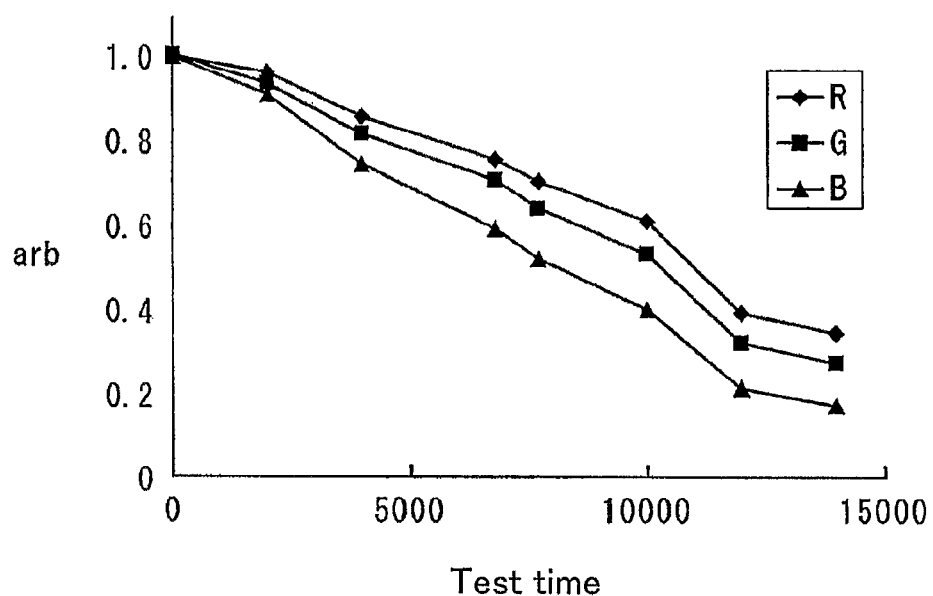
FIG. 8 is a graph showing the output of an RGB sensor of the oil state sensor in an experiment performed according to the configuration of FIG. 7.

FIG. 8 is a graph showing the output of the RGB sensor of the oil state sensor in an experiment performed according to the configuration of FIG. 7.

In FIG. 8, the unit of the ordinate axis is an arbitrary unit in which the maximum value of each of the R, G, and B values of a color detected by the RGB sensor of the oil state sensor is defined as 1 whereas the minimum value thereof is defined as 0.

As shown in FIG. 8, each of the R, G, and B values of the color detected by the RGB sensor of the oil state sensor becomes smaller correspondingly to the lapse of time of the experiment.

Figure 9:
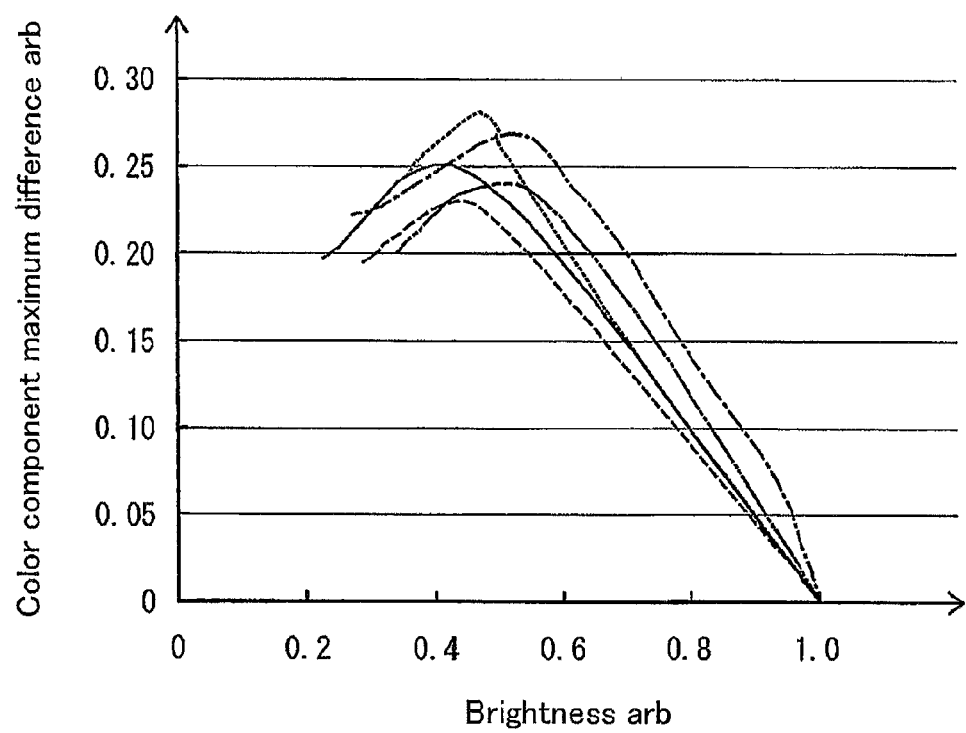
FIG. 9 is a graph showing results of the experiment performed according to the configuration of FIG. 7.

FIG. 9 is a graph showing results of the experiment performed according to the configuration of FIG. 7.

In FIG. 9, the unit of the ordinate axis is an arbitrary unit in which the maximum value of the color component maximum difference is defined as 1 whereas the minimum value thereof is defined as 0. The unit of the abscissa axis is an arbitrary unit in which the maximum value of brightness is defined as 1 whereas the minimum value thereof is defined as 0.

In FIG. 9, results of the experiment performed five times until the speed reducer 91 broke down are shown. Each graph in FIG. 9 shows an each-time result of the experiment. In fact, the number of times the experiment is performed is not limited to five, and the appropriateness of the lubricating-oil-deterioration state determination threshold value 84b and the appropriateness of the speed-reducer-breakage state determination threshold value 84c become better in proportion to an increase in the number of times the experiment is performed.

As shown in FIG. 9, when the experiment was started, each of the R, G, and B values of the color detected by the RGB sensor of the oil state sensor was equal to the full-scale maximum value of the output, and therefore the brightness was 1.0, and the color component maximum difference was 0.

According to the experimental results of FIG. 9, the brightness continued to become lower in proportion to the deterioration of the lubricating oil until the speed reducer 91 broke down.

On the other hand, the color component maximum difference continued to become greater in proportion to the deterioration of the lubricating oil in the early stage, and continued to become smaller in proportion to the deterioration of the lubricating oil from a certain time point until the speed reducer 91 broke down.

Figure 10:
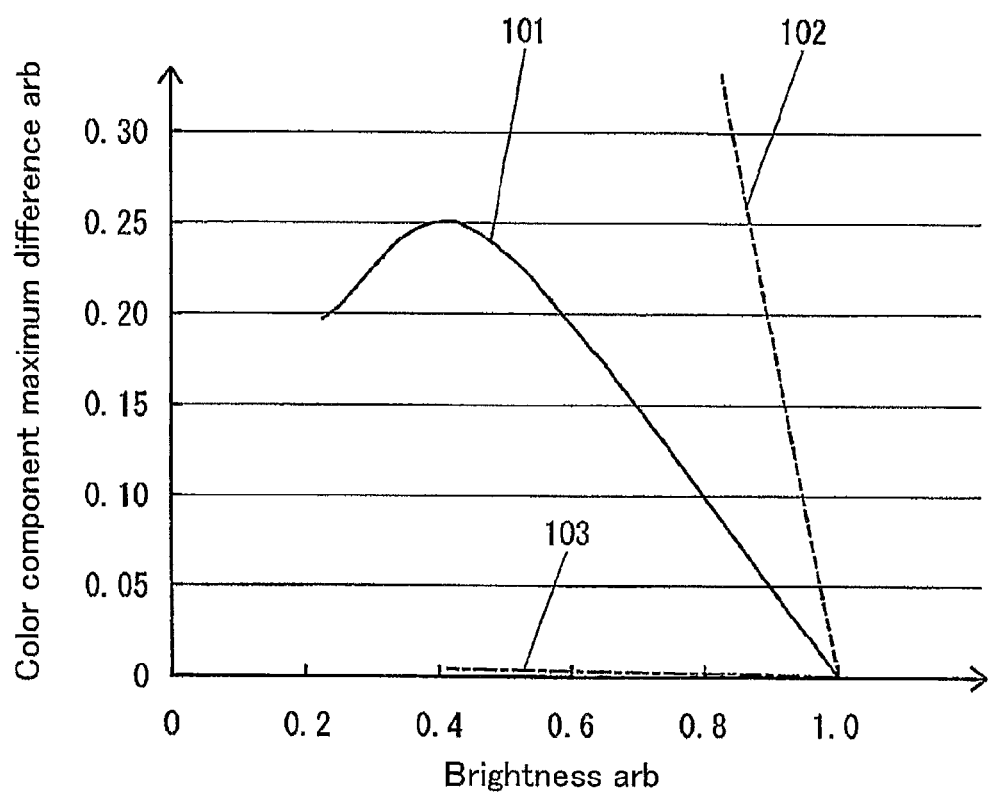
FIG. 10 is a graph showing an example of a relationship between brightness and a color component maximum difference that are calculated by the computer of FIG. 2.

FIG. 10 is a graph showing an example of a relationship between brightness and a color component maximum difference that are calculated by the computer 80.

In FIG. 10, the unit of the ordinate axis is an arbitrary unit in which the maximum value of the color component maximum difference is defined as 1 whereas the minimum value thereof is defined as 0. The unit of the abscissa axis is an arbitrary unit in which the maximum value of the brightness is defined as 1 whereas the minimum value thereof is defined as 0.

As described above, the shape of the graph showing a relationship between brightness and a color component maximum difference that are calculated by the computer 80 based on the output of the RGB sensor 73 of the oil state sensor 50 is formed like that of a graph 101 shown in FIG. 10.

A graph 102 shows a result of an experiment performed in a state in which the temperature of the lubricating oil 40a was kept invariably high without driving the speed reducer 40. When the temperature of the lubricating oil 40a was kept invariably high without driving the speed reducer 40, i.e., when the lubricating oil 40a was gradually deteriorated only by heat, the shape of the graph showing a relationship between brightness and a color component maximum difference that were calculated by the computer 80 based on the output of the RGB sensor 73 of the oil state sensor 50 was formed like that of the graph 102. In the graph 102, the brightness continued to decrease correspondingly to the deterioration of the lubricating oil 40a. The color component maximum difference continued to increase correspondingly to the deterioration of the lubricating oil 40a. However, the amount of increase in the color component maximum difference with respect to the amount of decrease in the brightness was extremely larger than in the early stage of the graph 101. In other words, it has become clear by the experiment that, when the lubricating oil 40a is oxidized and deteriorated by heat, an increase occurs mainly in the color component maximum difference with respect to changes in the brightness and in the color component maximum difference.

A graph 103 shows a result of an experiment in which the amount of impurities mixed with the lubricating oil 40a was increased without driving the speed reducer 40. When the amount of impurities mixed with the lubricating oil 40a was increased without driving the speed reducer 40, i.e., when the lubricating oil 40a was deteriorated only by mixing impurities therewith, the shape of the graph showing a relationship between brightness and a color component maximum difference that were calculated by the computer 80 based on the output of the RGB sensor 73 of the oil state sensor 50 was formed like that of the graph 103. In the graph 103, the brightness continued to decrease correspondingly to the deterioration of the lubricating oil 40a. The color component maximum difference continued to increase correspondingly to the deterioration of the lubricating oil 40a. However, the amount of increase in the color component maximum difference with respect to the amount of decrease in the brightness was extremely smaller than in the early stage of the graph 101. In other words, it has become clear by the experiment that, when the lubricating oil 40a is deteriorated by being mixed with impurities, a decrease occurs mainly in the brightness with respect to changes in the brightness and in the color component maximum difference.

The inventors of the present invention have found out through the aforementioned experiment that the deterioration state of the lubricating oil 40a of the speed reducer 40 has a strong correlation with the brightness of the color of light detected by the RGB sensor 73 and the color component maximum difference.

Figure 11:
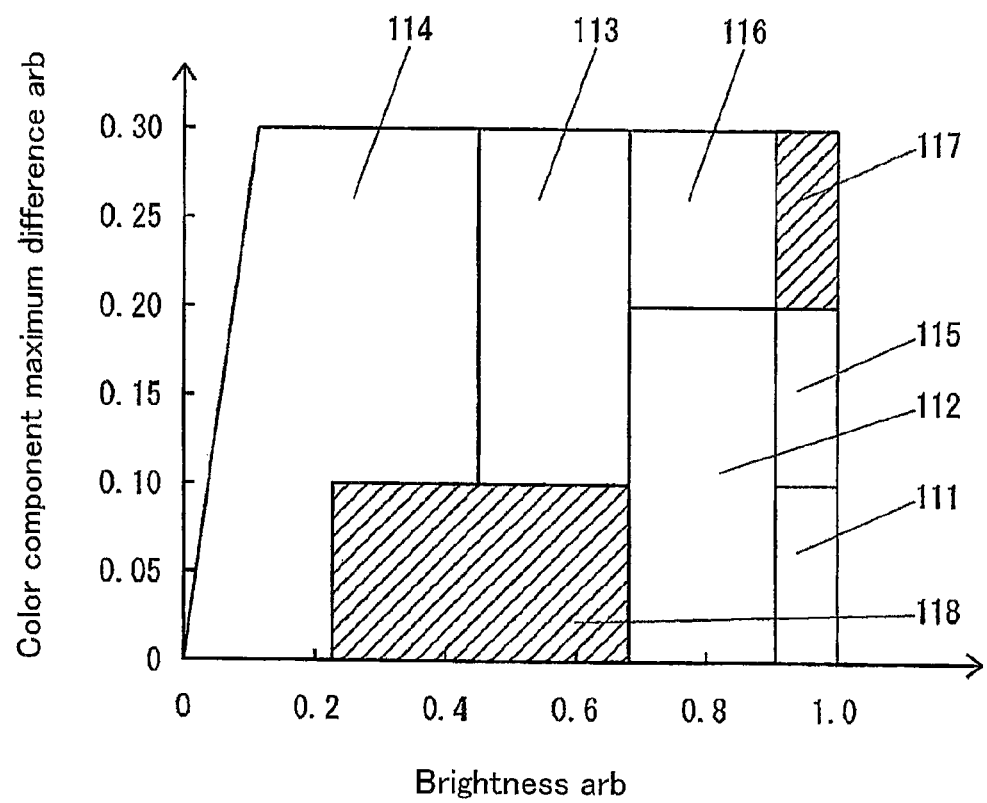
FIG. 11 is a diagram explaining an example of a threshold value used to determine the deterioration state of lubricating oil shown in FIG. 6 when the color component calculation value is a color component maximum difference.

FIG. 11 is a diagram for explaining an example of a lubricating-oil-deterioration state determination threshold value 84b when the color component calculation value is a color component maximum difference.

In FIG. 11, the unit of the ordinate axis is an arbitrary unit in which the maximum value of the color component maximum difference is defined as 1 whereas the minimum value thereof is defined as 0. The unit of the abscissa axis is an arbitrary unit in which the maximum value of brightness is defined as 1 whereas the minimum value thereof is defined as 0.

A person who determines the lubricating-oil-deterioration state determination threshold value 84b divides possible combinations of the brightness and the color component maximum difference of a color detected by the RGB sensor 73 of the oil state sensor 50 correspondingly to the deterioration of the lubricating oil 40a into, for example, eight ranges 111 to 118 based on the experimental results mentioned above as shown in FIG. 11. The range 111 is a range in which the lubricating oil 40a is presumed to undergo no deterioration. The range 112 is a range in which the deterioration level of the lubricating oil 40a is presumed to be low. The range 113 is a range in which the deterioration level of the lubricating oil 40a is presumed to be intermediate. The range 114 is a range in which the deterioration level of the lubricating oil 40a is presumed to be high. The range 115 and the range 116 are ranges in which the lubricating oil 40a itself is presumed to be oxidized by heat and be deteriorated. The range 117 is a range in which the lubricating oil 40a itself is presumed to be oxidized by heat and be abnormally deteriorated. The range 118 is a range in which the lubricating oil 40a itself is presumed to be abnormally deteriorated by being mixed with impurities.

The ranges 111, 112, 113, and 114 are determined based on experimental results according to the configuration of FIG. 7. The ranges 115, 116, and 117 are determined based on experimental results according to the configuration of FIG. 7 and results of an experiment in which the temperature of the lubricating oil 40a was kept invariably high without driving the speed reducer 40. The range 118 is determined based on experimental results according to the configuration of FIG. 7 and results of an experiment in which the amount of impurities mixed with the lubricating oil 40a was increased without driving the speed reducer 40.

The lubricating-oil-deterioration state determination threshold value 84b is determined such that it can decide in which one of the ranges 111 to 118 the brightness and the color component maximum difference of a color detected by the RGB sensor 73 of the oil state sensor 50 exist.

The experimental results mentioned above vary according to the type of the speed reducer 40 and the kind of the lubricating oil 40a. Therefore, the lubricating-oil-deterioration state determination threshold value 84b is determined depending on the type of the speed reducer 40 and the kind of the lubricating oil 40a.

Next, a method for determining a speed-reducer-breakage state determination threshold value 84c will be described.

The inventors of the present invention have found out through an experiment performed according to the configuration of FIG. 7 that the state of the breakage of the speed reducer 40 has a strong correlation with the brightness and the color component maximum difference of the color of light detected by the RGB sensor 73.

Figure 12:
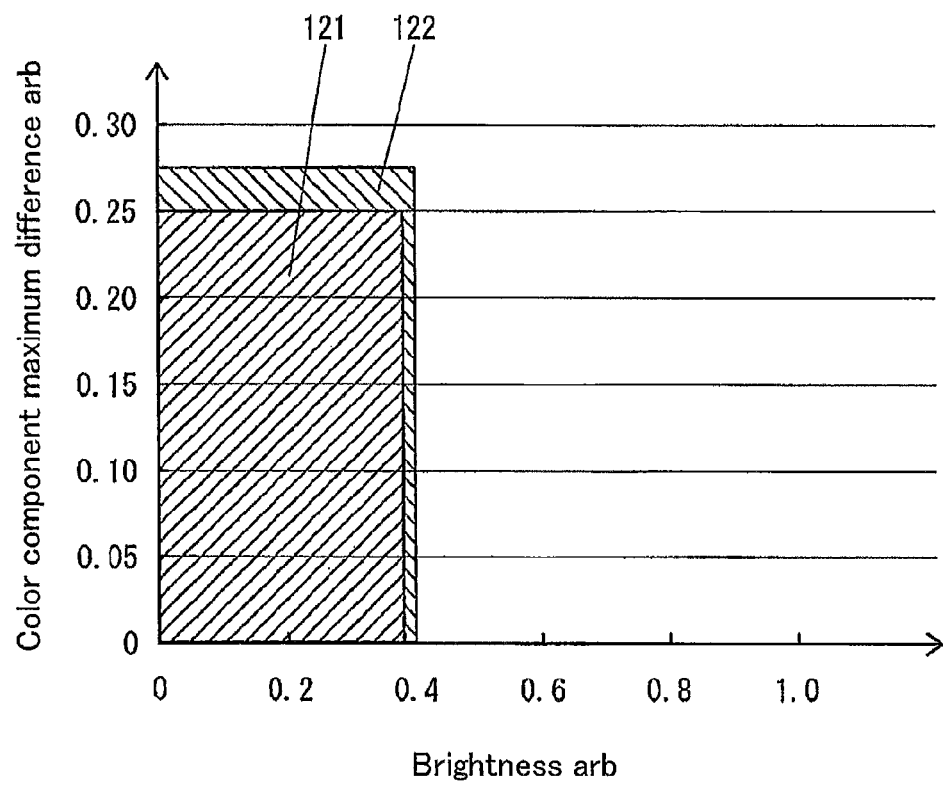
FIG. 12 is a diagram explaining an example of a threshold value used to determine the breakage state of a speed reducer shown in FIG. 6 when the color component calculation value is a color component maximum difference.

FIG. 12 is a diagram explaining an example of the speed-reducer-breakage state determination threshold value 84c when the color component calculation value is a color component maximum difference.

In FIG. 12, the unit of the ordinate axis is an arbitrary unit in which the maximum value of the color component maximum difference is defined as 1 whereas the minimum value thereof is defined as 0. The unit of the abscissa axis is an arbitrary unit in which the maximum value of the brightness is defined as 1 whereas the minimum value thereof is defined as 0.

Based on experimental results obtained according to the configuration of FIG. 7, a person who determines the speed-reducer-breakage state determination threshold value 84c determines a range 121 of a combination in which the speed reducer 40 is presumed to have broken down and a range 122 of a combination in which the speed reducer 40 is presumed to require an overhaul and repair although the speed reducer 40 has not broken down among possible combinations of the brightness and the color component maximum difference of a color detected by the RGB sensor 73 of the oil state sensor 50 correspondingly to the deterioration of the lubricating oil 40a.

The speed-reducer-breakage state determination threshold value 84c is determined such that it is possible to determine whether the brightness and the color component maximum difference of a color detected by the RGB sensor 73 of the oil state sensor 50 exist in the range 121 or in the range 122.

Experimental results obtained according to the configuration of FIG. 7 vary according to the type of the speed reducer 40 and the kind of the lubricating oil 40a. Therefore, the speed-reducer-breakage state determination threshold value 84c is determined depending on the type of the speed reducer 40 and the kind of the lubricating oil 40a.

Next, the operation of the joint portion 32 of the industrial robot 20 will be described. Although the joint portion 32 is hereinafter described, the same applies to the joint portions 31 and 33 to 36.

When the output shaft of the motor 49 of the joint portion 32 rotates, the rotational force of the motor 49 is decreased by the speed reducer 40, and moves the arm 23 fixed to the supporter 42 of the speed reducer 40 with respect to the arm 22 fixed to the case 41 of the speed reducer 40.

Next, the operation of the oil state sensor 50 will be described.

The oil state sensor 50 emits white light from the white LED 72 by means of electric power supplied from an external device through the waterproof connector 76.

Thereafter, the oil state sensor 50 outputs the light quantity of each of the RGB colors of light received by the RGB sensor 73 as an electric signal through the waterproof connector 76 to an external device.

It is also possible for the oil state sensor 50 to output temperature detected by the temperature sensor 78 as an electric signal through the waterproof connector 76 to the external device.

The oil state sensor 50 may be provided with additional sensors other than the RGB sensor 73 and the temperature sensor 78. It is also possible for the oil state sensor 50 to output a detection result obtained from such additional sensors as an electric signal through the waterproof connector 76 to the external device.

It is possible for the computer 80 to determine the kind and the amount of contaminants in the lubricating oil 40a of the speed reducer 40 based on a color detected by the RGB sensor 73. In other words, it is possible for the oil state sensor 50 to detect the degree of deterioration of the lubricating oil 40a by detecting the color of contaminants contained in the lubricating oil 40a.

Next, adjustment of the output of the RGB sensor 73 of the oil state sensor 50 will be described.

It is possible for a user of the oil state sensor 50 to cause the computer 80 to obtain an R value, a G value, and a B value of a color detected by the RGB sensor 73 of the oil state sensor 50 in a state in which light emitted by the white LED 72 is blocked in the oil receiving gap 60a. In other words, it is possible for the computer 80 to obtain an R value, a G value, and a B value of a color detected by the RGB sensor 73 in a state in which the arrival of light emitted by the white LED 72 at the RGB sensor 73 has been intercepted.

Additionally, it is possible for a user of the oil state sensor 50 to cause the computer 80 to obtain an R value, a G value, and a B value of a color detected by the RGB sensor 73 in a state in which the lubricating oil 40a has not been used. In other words, it is possible for the computer 80 to obtain an R value, a G value, and a B value of a color detected by the RGB sensor 73 in a state in which the lubricating oil 40a has been introduced in the speed reducer 40.

Thereafter, the computer 80 adjusts the output of the RGB sensor 73 in accordance with commands issued by a user of the oil state sensor 50 such that the R value, the G value, and the B value of the color detected by the RGB sensor 73 become full-scale minimum values of the output, respectively, i.e., become black in a state in which the arrival of light emitted by the white LED 72 at the RGB sensor 73 has been intercepted and such that the R value, the G value, and the B value of the color detected by the RGB sensor 73 become full-scale maximum values of the output, respectively, i.e., become white in a state in which the lubricating oil 40a has been introduced in the speed reducer 40. In other words, the computer 80 adjusts the output of the RGB sensor 73 of the oil state sensor 50 such that the output of the RGB sensor 73 at the time when the arrival of light emitted by the white LED 72 at the RGB sensor 73 is intercepted becomes black and such that the output of the RGB sensor 73 at the time when the lubricating oil 40a is introduced into the speed reducer 40 becomes white.

Next, a state determining method according to the present embodiment will be described.

Figure 13:
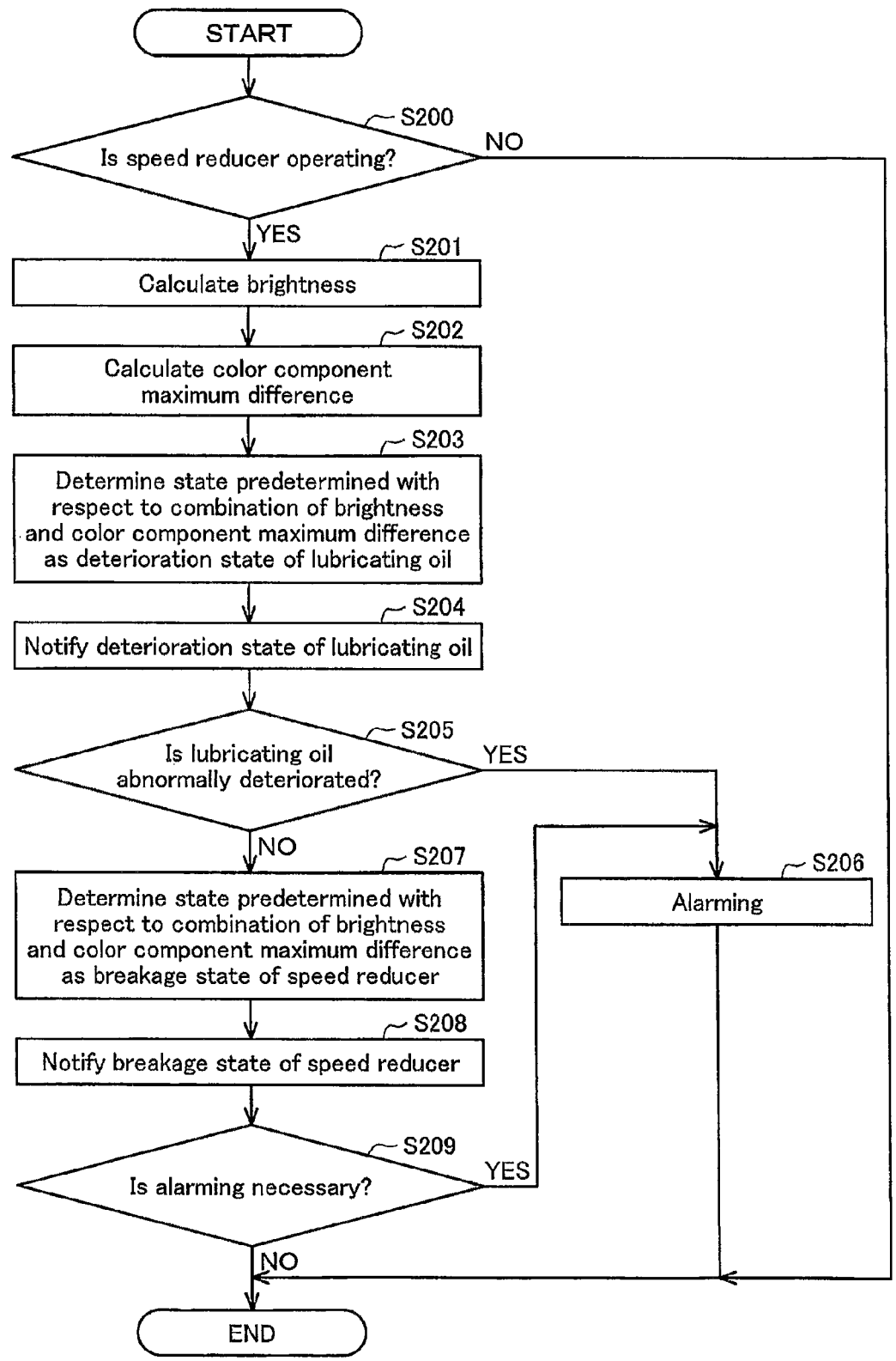
FIG. 13 is a flowchart of the operation of the computer of FIG. 2.

FIG. 13 is a flowchart of the operation of the computer 80.

The computer 80 performs an operation shown in FIG. 13 for each of a plurality of oil state sensors 50 included in the industrial robot 20. The operation of the computer 80 with respect to a single oil state sensor 50 will be hereinafter described.

The computer 80 executes the state determining program 84a, and hence performs the operation of FIG. 13 at predetermined time intervals for each oil state sensor 50. It is possible for a user of the computer 80 to set the time intervals arbitrarily, e.g., at time intervals of six hours.

As shown in FIG. 13, the operation situation determining means 85e of the control portion 85 of the computer 80 determines whether the speed reducer 40 is operating (S200). When the temperature of the lubricating oil 40a detected by the temperature sensor 78 is higher than or equal to a predetermined temperature, the operation situation determining means 85e determines that the speed reducer 40 is operating, and, when the temperature of the lubricating oil 40a detected by the temperature sensor 78 is less than the predetermined temperature, the operation situation determining means 85e determines that the speed reducer 40 is operating.

The brightness calculating means 85a of the control portion 85 calculates the brightness of a color detected by the RGB sensor 73 when it is determined in S200 that the speed reducer 40 is operating (S201). In other words, it is possible for the brightness calculating means 85a to calculate brightness according to the expression 1 by use of each of the R, G, and B values of the color detected by the RGB sensor 73.

Thereafter, the color-component calculation value calculating means 85b of the control portion 85 calculates a color component maximum difference, which is the difference between the maximum value and the minimum value among the R, G, and B values of the color detected by the RGB sensor 73 (S202). In other words, it is possible for the color-component calculation value calculating means 85b to calculate a color component maximum difference according to the expression 2 by use of each of the R, G, and B values of the color detected by the RGB sensor 73.

Thereafter, based on the lubricating-oil-deterioration state determination threshold value 84b, the state determining means 85c of the control portion 85 decides in which one of the ranges 111 to 118 of FIG. 11 a combination of the brightness calculated in S201 and the color component maximum difference calculated in S202 exists. In other words, the state determining means 85c determines that the deterioration state of the lubricating oil 40a is a state predetermined with respect to a combination of the brightness calculated in S201 and the color component maximum difference calculated in S202 (S203).

For example, when a combination of the brightness calculated in S201 and the color component maximum difference calculated in S202 exists in the range 111, the state determining means 85c determines that the lubricating oil 40a has undergone no deterioration. When a combination of the brightness calculated in S201 and the color component maximum difference calculated in S202 exists in the range 112, the state determining means 85c determines that the deterioration level of the lubricating oil 40a is low. When a combination of the brightness calculated in S201 and the color component maximum difference calculated in S202 exists in the range 113, the state determining means 85c determines that the deterioration level of the lubricating oil 40a is intermediate. When a combination of the brightness calculated in S201 and the color component maximum difference calculated in S202 exists in the range 114, the state determining means 85c determines that the deterioration level of the lubricating oil 40a is high. When a combination of the brightness calculated in S201 and the color component maximum difference calculated in S202 exists in the range 115 or in the range 116, the state determining means 85c determines that the lubricating oil 40a itself is oxidized by heat and is deteriorated. When a combination of the brightness calculated in S201 and the color component maximum difference calculated in S202 exists in the range 117, the state determining means 85c determines that the lubricating oil 40a itself is oxidized by heat and is abnormally deteriorated. When a combination of the brightness calculated in S201 and the color component maximum difference calculated in S202 exists in the range 118, the state determining means 85c determines that the lubricating oil 40a is abnormally deteriorated by being mixed with impurities.

Thereafter, the state notifying means 85d of the control portion 85 notifies the deterioration state of the lubricating oil 40a determined in S203 to, for example, the display portion 82 of FIG. 14 (S204).

FIG. 14 is a diagram showing an example of the display of the display portion 82.

In FIG. 14, the deterioration state of the lubricating oil 40a of the speed reducer A is displayed as "No deterioration." The deterioration state of the lubricating oil 40a of the speed reducer B and that of the speed reducer C are each displayed as "Deterioration level High." The deterioration state of the lubricating oil 40a of the speed reducer D is displayed as "Abnormal by being mixed with Impurities."

As shown in FIG. 13, after completing the process of step S204, the state notifying means 85d determines whether the lubricating oil 40a is abnormally deteriorated (S205). When it is determined in S204 that the lubricating oil 40a itself is oxidized by heat and is abnormally deteriorated or when it is determined in S204 that the lubricating oil 40*a* is abnormally deteriorated by being mixed with impurities, the state notifying means 85*d* determines that the lubricating oil 40*a* is abnormally deteriorated.

When it is determined in S205 that the lubricating oil 40*a* is abnormally deteriorated, the state notifying means 85*d* performs alarming, for example, by inverting colors on the display of the display portion 82 (S206).

In the display of FIG. 14, alarming is performed by inverting colors of the deterioration state of the lubricating oil 40*a* of the speed reducer D. Therefore, it is possible for a user of the computer 80 to easily recognize that a large amount of impurities, such as sludge or wear-out powder, have been mixed with the lubricating oil 40*a* because of, for example, the breakdown of the speed reducer D.

As shown in FIG. 13, when the state notifying means 85*d* does not determine in S205 that the lubricating oil 40*a* is abnormally deteriorated, the state determining means 85*c* determines, based on the speed-reducer-breakage state determination threshold value 84*c*, whether a combination of the brightness calculated in S201 and the color component maximum difference calculated in S202 exists in the range 121 or in the range 122 of FIG. 12. In other words, the state determining means 85*c* determines that the breakage state of the speed reducer 40 is a state predetermined with respect to a combination of the brightness calculated in S201 and the color component maximum difference calculated in S202 (S207).

For example, when a combination of the brightness calculated in S201 and the color component maximum difference calculated in S202 exists in the range 121, the state determining means 85*c* determines that the speed reducer 40 has broken down. When a combination of the brightness calculated in S201 and the color component maximum difference calculated in S202 exists in the range 122, the state determining means 85*c* determines that the speed reducer 40 require an overhaul and repair. When a combination of the brightness calculated in S201 and the color component maximum difference calculated in S202 exists neither in the range 121 nor in the range 122, the state determining means 85*c* determines that the speed reducer 40 has not broken down.

Thereafter, the state notifying means 85*d* of the control portion 85 notifies the breakage state of the speed reducer 40 determined in S207 to the display portion 82, for example, as "State of Speed Reducer" as shown in FIG. 14 (S208).

In FIG. 14, the state of the speed reducer A is displayed as "Normal." The state of the speed reducer B is displayed as "Require Overhaul and Repair." The state of the speed reducer C is displayed as "Breakdown." Concerning the speed reducer D, the lubricating oil 40*a* is abnormally deteriorated, and therefore the state of the speed reducer is not displayed.

As shown in FIG. 13, after completing the process of step S208, the state notifying means 85*d* determines whether alarming is necessary (S209). When it is determined in S207 that the speed reducer 40 requires an overhaul and repair or when it is determined in S207 that the speed reducer 40 has broken down, the state notifying means 85*d* determines that alarming is necessary.

When it is determined in S209 that alarming is necessary, the state notifying means 85*d* performs alarming, for example, by inverting colors on the display of the display portion 82 (S206).

In the display of FIG. 14, alarming is performed by inverting colors of the state of the speed reducer B and the state of the speed reducer C. Therefore, it is possible for a user of the computer 80 to easily recognize that the speed reducer B requires an overhaul and repair or that the speed reducer C has broken down.

As shown in FIG. 13, when it is determined in S200 that the speed reducer 40 is not operating or when it is determined in S209 that the process of step S206 has been completed or that alarming is not necessary, the control portion 85 ends the process of FIG. 13.

As described above, the state determining method according to the present embodiment determines the deterioration state of the lubricating oil 40*a* of the speed reducer 40 based on the brightness and the color component maximum difference of the color of light detected by the RGB sensor 73 (S203), and therefore it is possible to determine the deterioration state of the lubricating oil 40*a* of the speed reducer 40 instantly and with higher accuracy than conventional methods.

When necessary, various additives are added to the lubricating oil 40*a*, which include a friction reducing agent to reduce the friction of a friction surface, such as organic molybdenum (Mo) including molybdenum dithiocarbamate (MoDTC) and molybdenum dithiophosphate (MoDTP), an extreme-pressure additive, such as an SP-based addition agent, to improve extreme-pressure properties serving as a capability for restraining the burning of a friction surface, and a dispersing agent, such as Ca sulfonate, to restrain the generation or adhesion of sludge. For example, these additives are adhered to or are united to or are precipitated to the metal surface of the industrial robot 20 and of the speed reducer 40, and are separated from the lubricating oil 40*a* correspondingly to the deterioration of the lubricating oil 40*a*. Based on a detected color, the oil state sensor 50 is capable of determining not only the amount of iron powder contained in the lubricating oil 40*a* but also the deterioration level of base oil, which corresponds to the decrease of various additives that have been added to the lubricating oil 40*a*, and also the increase of contaminants such as sludge.

The state determining method according to the present embodiment determines the deterioration state of the lubricating oil 40*a* of the speed reducer 40 based on a combination of the brightness and the color component maximum difference of the color of light detected by the RGB sensor 73 (S203), and therefore there is no need to perform a complicated process in order to determine the deterioration state of the lubricating oil 40*a* of the speed reducer 40. Therefore, the state determining method according to the present embodiment is capable of lessening a burden imposed to determine the deterioration state of the lubricating oil 40*a* of the speed reducer 40.

In general, in industrial robots, the accuracy of an arm trajectory is greatly influenced by the performance of speed reducers used at joint portions. Therefore, it is important for a speed reducer for an industrial robot to be appropriately replaced by another when its performance falls. However, when the speed reducer for the industrial robot is replaced, the industrial robot including the speed reducer or a production line at which the industrial robot is installed must be stopped. Therefore, adequate prediction of breakdown of the speed reducer for the industrial robot is greatly important in order to determine the replacement time of the speed reducer for the industrial robot.

The state determining method according to the present embodiment determines the breakage state of the speed reducer 40 based on the brightness and the color component maximum difference of the color of light detected by the RGB sensor 73 (S207), and therefore it is possible to determine the breakage state of the speed reducer 40 instantly and with higher accuracy than conventional methods.

It is possible to further improve the prediction accuracy of the breakdown of the speed reducer 40 by employing together the color of light detected by the RGB sensor 73 of the oil state sensor 50 and the temperature sensor 78, which measures the temperature of the lubricating oil 40a, or a monitoring mechanism that monitors the electric current value of the motor 49, for example.

Additionally, the state determining method according to the present embodiment determines the breakage state of the speed reducer 40 based on a combination of the brightness and the color component maximum difference of the color of light detected by the RGB sensor 73 (S207), and therefore there is no need to perform a complicated process in order to determine the breakage state of the speed reducer 40. Therefore, the state determining method according to the present embodiment is capable of reducing a burden imposed to determine the breakage state of the speed reducer 40.

Additionally, when a color component maximum difference is calculated (S202), the state determining method according to the present embodiment calculates the color component maximum difference while determining which value is the maximum and which value is the minimum among the R, G, and B values of the color of light detected by the RGB sensor 73 each time. However, it has been proved by experiments that the maximum value is normally the R value among the R, G, and B values of the color detected by the RGB sensor 73 (see FIG. 8). It has also been proved by experiments that the minimum value is normally the B value among the R, G, and B values of the color detected by the RGB sensor 73 (see FIG. 8). Therefore, in the state determining method according to the present embodiment, the color-component calculation value calculating means 85b may be configured to calculate a difference between the R and B values of the color detected by the RGB sensor 73 as a color component maximum difference in S202. If this configuration is employed, the state determining method according to the present embodiment is not required to determine which value is the maximum and which value is the minimum among the R, G, and B values of the color detected by the RGB sensor 73 each time, and therefore it is possible to reduce a burden imposed to calculate the color component maximum difference.

Additionally, in the state determining method according to the present embodiment, the output of the RGB sensor 73 is adjusted for each lubricating oil 40a such that the output of the RGB sensor 73 at the time when the arrival of light at the RGB sensor 73 is intercepted becomes black and such that the output of the RGB sensor 73 at the time when the lubricating oil 40a is introduced into the speed reducer 40 becomes white, and therefore it is possible to reduce the influence of individual differences of the lubricating oil 40a upon state determination.

When the lubricating oil 40a is changed, brightness calculated by the brightness calculating means 85a becomes greatly higher after changing the lubricating oil 40a than the lubricating oil 40a that has not yet been changed. Therefore, based on a change in brightness calculated by the brightness calculating means 85a, the control portion 85 of the computer 80 is capable of automatically determining that the lubricating oil 40a has been changed. When the lubricating oil 40a is changed, each of the R, G, and B values of a color detected by the RGB sensor 73 also becomes greatly higher after changing the lubricating oil 40a than the lubricating oil 40a that has not yet been changed although brightness has been described above. Therefore, likewise, based on the change of any one of the R, G, and B values of a color detected by the RGB sensor 73, the control portion 85 of the computer 80 is capable of automatically determining that the lubricating oil 40a has been changed.

When the speed reducer 40 is operating (YES in S200), i.e., when the lubricating oil 40a of the speed reducer 40 is stirred by the operation of the speed reducer 40 so that impurities contained in the lubricating oil 40a are caused to be evenly present in the lubricating oil 40a, the state determining method according to the present embodiment calculates the brightness of the color detected by the RGB sensor 73 (S201), and calculates the color component maximum difference, which is the difference between the maximum value and the minimum value among the R, G, and B values of the color detected by the RGB sensor 73 (S202), and therefore the accuracy of the brightness calculated in S201 and the accuracy of the color component maximum difference calculated in S202 are improved. Therefore, the state determining method according to the present embodiment is capable of determining the deterioration state of the lubricating oil 40a with high accuracy (S203), and is capable of determining the breakage state of the speed reducer 40 with high accuracy (S207). However, in the state determining method according to the present embodiment, determination of whether the speed reducer 40 is operating may be excluded in the operation of FIG. 13.

When the speed reducer 40 is operating, the temperature of the lubricating oil 40a rises because of the operation of the speed reducer 40, and therefore, in the present embodiment, the operation situation determining means 85e determines whether the speed reducer 40 is operating based on the temperature of the lubricating oil 40a. However, based on information other than the temperature of the lubricating oil 40a, the operation situation determining means 85e may determine whether the speed reducer 40 is operating. For example, based on information, such as a signal from a vibration sensor attached to the speed reducer 40, a signal from an acceleration sensor attached to the speed reducer 40, and a signal showing a driving current of the motor 49 that drives the speed reducer 40, the operation situation determining means 85e may determine whether the speed reducer 40 is operating. When a machine subject to detection by the oil state sensor 50 is a machine driven not by the speed reducer 40 but by pneumatic pressure, the operation situation determining means 85e may determine whether the speed reducer 40 is operating based on a signal from a sensor that detects pneumatic pressure by which the machine is driven. When a machine subject to detection by the oil state sensor 50 is a machine driven by oil pressure, the operation situation determining means 85e may determine whether the speed reducer 40 is operating based on a signal from a sensor that detects oil pressure by which the machine is driven.

In the present embodiment, the operation situation determining means 85e determines whether the speed reducer 40 is operating based on temperature detected by the temperature sensor 78 fixed to the housing 51 of the oil state sensor 50. However, the operation situation determining means 85e may be configured to determine whether the speed reducer 40 is operating based on a temperature difference obtained by subtracting the temperature of air around the oil state sensor 50 detected by a temperature sensor (not shown) from the temperature detected by the temperature sensor 78. In this configuration, it is possible for the operation situation determining means 85e to exclude the amount of change influenced by the temperature of air around the oil state sensor 50 among changes in the temperature of the lubricating oil 40a, and therefore it is possible to even more accurately determine whether the speed reducer 40 is operating.

Preferably, the installation position of the oil state sensor 50 is appropriately set according to, for example, the purpose of use of the industrial robot 20 without being limited to the position shown in the present embodiment.

Additionally, for example, the oil state sensor 50 may use a battery as an electric power supply means.

Additionally, for example, the oil state sensor 50 may use wireless communications as an output means for outputting a detection result to an external device.

An example in which the color component calculation value, which is a value calculated based on the maximum value and the minimum value among the R, G, and B values of a color detected by the RGB sensor 73, is a color component maximum difference has been described above. However, in the state determining method according to the present embodiment, the color component calculation value may be a value other than the color component maximum difference. For example, in the state determining method according to the present embodiment, the color component calculation value may be a color component maximum ratio, which is the ratio between the maximum value and the minimum value among the R, G, and B values of a color detected by the RGB sensor 73, or may be an integral value of the brightness of the color component maximum difference (hereinafter, referred to as a "color component maximum difference integral value"), or may be an integral value of the brightness of the color component maximum ratio (hereinafter, referred to as a "color component maximum ratio integral value"), or may be a differential value by the brightness of the color component maximum difference, or may be a differential value by the brightness of the color component maximum ratio.

An example in which the color component calculation value is a color component maximum difference integral value will be hereinafter described.

The color-component calculation value calculating means 85b is capable of calculating a color component maximum difference integral value, which is an integral value of the brightness of a color component maximum difference as a color component calculation value by using each of the R, G, and B values of a color detected by the RGB sensor 73. More specifically, the color-component calculation value calculating means 85b is capable of calculating a color component maximum difference integral value such that, each time brightness calculated by the brightness calculating means 85a while using each of the R, G, and B values of the color detected by the RGB sensor 73 changes, a color component maximum difference, which is the difference between the maximum value and the minimum value among the R, G, and B values of the color detected by the RGB sensor 73, is added at that time.

Figure 15:
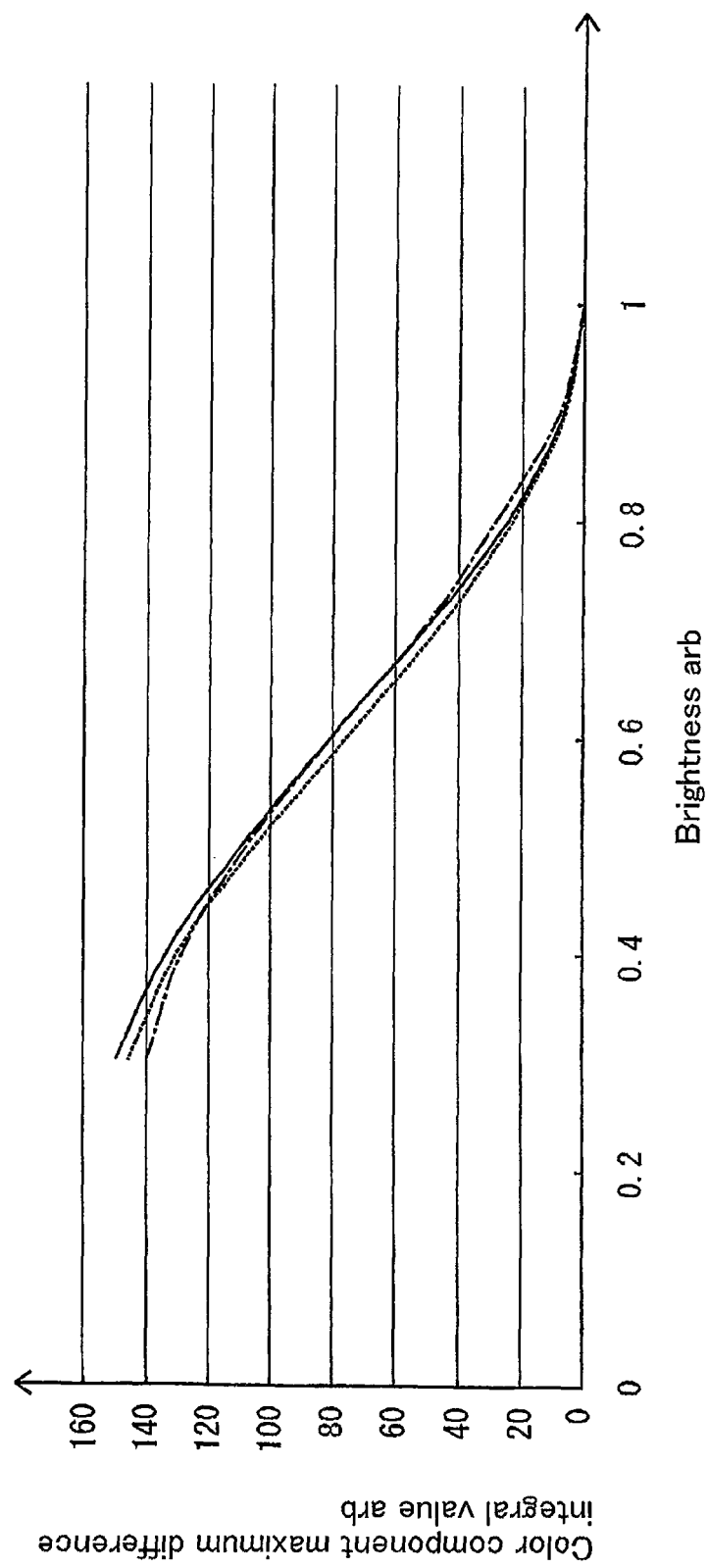
FIG. 15 is a graph showing an example of a relationship between brightness and a color component maximum difference integral value that are calculated by the computer of FIG. 2.

FIG. 15 is a graph showing an example of a relationship between brightness and a color component maximum difference integral value calculated by the computer 80.

In FIG. 15, the unit of the ordinate axis is an arbitrary unit. The unit of the abscissa axis is an arbitrary unit in which the maximum value of brightness is defined as 1 whereas the minimum value thereof is defined as 0.

Based on the output of the RGB sensor 73 of the oil state sensor 50, the shape of the graph showing a relationship between brightness and a color component maximum difference integral value calculated by the computer 80 is formed like three graphs shown in FIG. 15, for example.

FIG. 15 shows results of three experiments performed until the speed reducer 91 broke down. Each graph of FIG. 15 shows a result of each experiment. In fact, the number of times the experiment is performed is not limited to three, and the appropriateness of a lubricating-oil-deterioration state determination threshold value 84b and that of a speed-reducer-breakage state determination threshold value 84c become higher in proportion to an increase in the number of times the experiment is performed.

As shown in FIG. 15, when the experiment was started, each of the R, G, and B values of the color detected by the RGB sensor of the oil state sensor was a full-scale maximum value of output, and therefore the brightness was 1.0. When the experiment was started, the color component maximum difference integral value was 0.

According to the experimental results of FIG. 15, the brightness continued to decrease correspondingly to the deterioration of the lubricating oil until the speed reducer 91 broke down.

On the other hand, the color component maximum difference integral value continued to increase correspondingly to the deterioration of the lubricating oil until the speed reducer 91 broke down.

Next, a method for determining a lubricating-oil-deterioration state determination threshold value 84b will be described.

The inventors of the present invention have found out through the same experiment as the aforementioned experiment concerning the color component maximum difference that the deterioration state of the lubricating oil 40a of the speed reducer 40 has a strong correlation with the brightness and the color component maximum difference integral value of the color of light detected by the RGB sensor 73.

Figure 16:
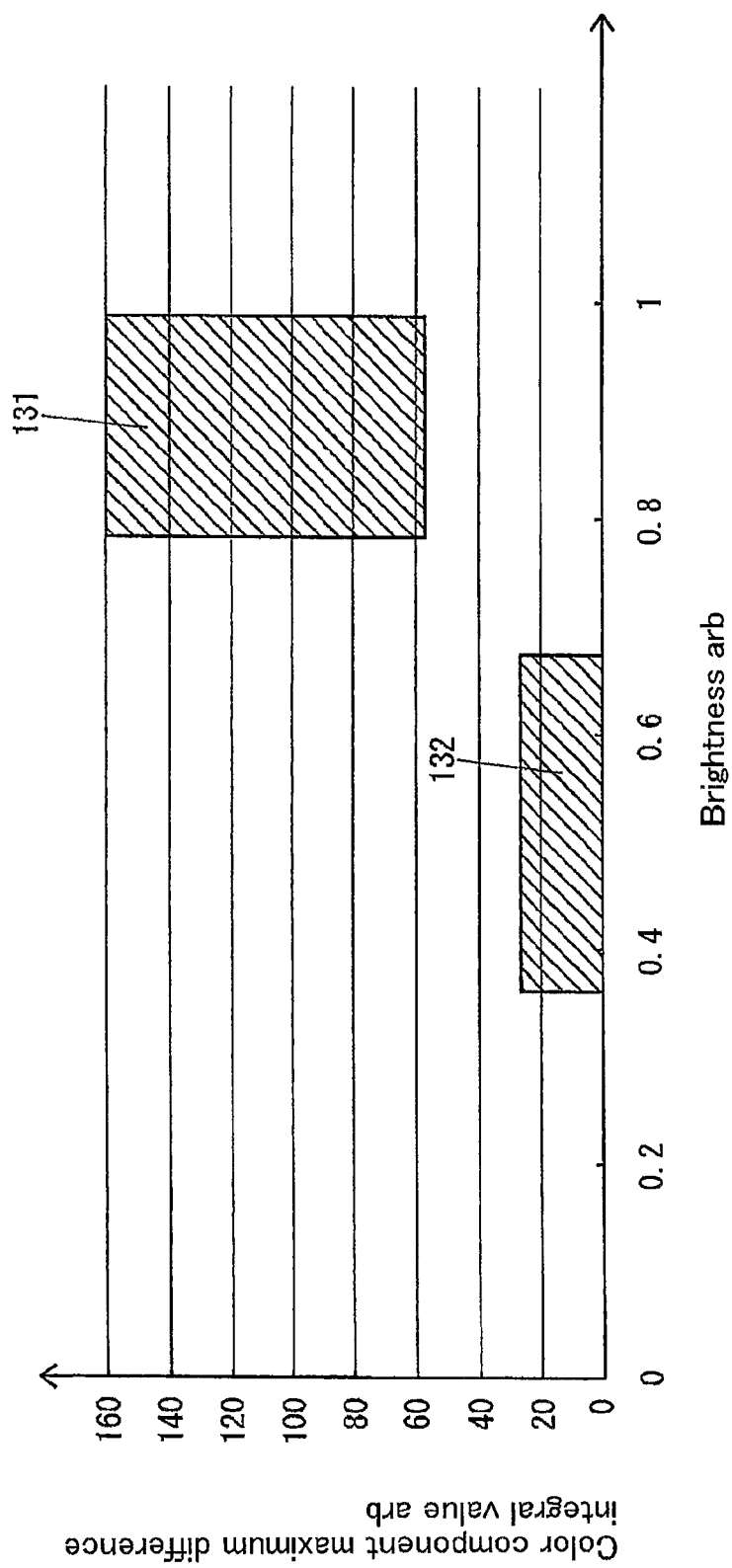
FIG. 16 is a diagram explaining an example of a threshold value used to determine the deterioration state of lubricating oil shown in FIG. 6 when the color component calculation value is a color component maximum difference integral value.

FIG. 16 is a diagram explaining an example of a lubricating-oil-deterioration state determination threshold value 84b when the color component calculation value is a color component maximum difference integral value.

In FIG. 16, the unit of the ordinate axis is an arbitrary unit. The unit of the abscissa axis is an arbitrary unit in which the maximum value of brightness is defined as 1 whereas the minimum value thereof is defined as 0.

Based on the aforementioned experimental results, a person who determines the lubricating-oil-deterioration state determination threshold value 84b divides, into a plurality of ranges, possible combinations of the brightness and the color component maximum difference integral value of a color detected by the RGB sensor 73 of the oil state sensor 50 correspondingly to the deterioration of the lubricating oil 40a. The range 131 is a range in which the lubricating oil 40a itself is presumed to be oxidized by heat and be abnormally deteriorated. The range 132 is a range in which the lubricating oil 40a is presumed to be abnormally deteriorated by being mixed with impurities. Other ranges, such as a range in which the lubricating oil 40a is presumed to undergo no deterioration, a range in which the deterioration level of the lubricating oil 40a is presumed to be low, a range in which the deterioration level of the lubricating oil 40a is presumed to be intermediate, and a range in which the deterioration level of the lubricating oil 40a is presumed to be high, are also provided in the same way as in the example of FIG. 11 although these are not shown in FIG. 16.

The lubricating-oil-deterioration state determination threshold value 84b is determined such that it is possible to decide in which one of the ranges including the ranges 131 and 132 the brightness and the color component maximum difference integral value of the color detected by the RGB sensor 73 of the oil state sensor 50 exist.

The aforementioned experimental results vary according to the type of the speed reducer 40 and the kind of the lubricating oil 40a. Therefore, the lubricating-oil-deterioration state determination threshold value 84b is determined depending on the type of the speed reducer 40 and the kind of the lubricating oil 40a.

Next, a method for determining a speed-reducer-breakage state determination threshold value 84c will be described.

The inventors of the present invention have found out through the same experiment as the aforementioned experiment concerning the color component maximum difference that the breakage state of the speed reducer 40 has a strong correlation with the brightness and the color component maximum difference integral value of the color of light detected by the RGB sensor 73.

Figure 17:
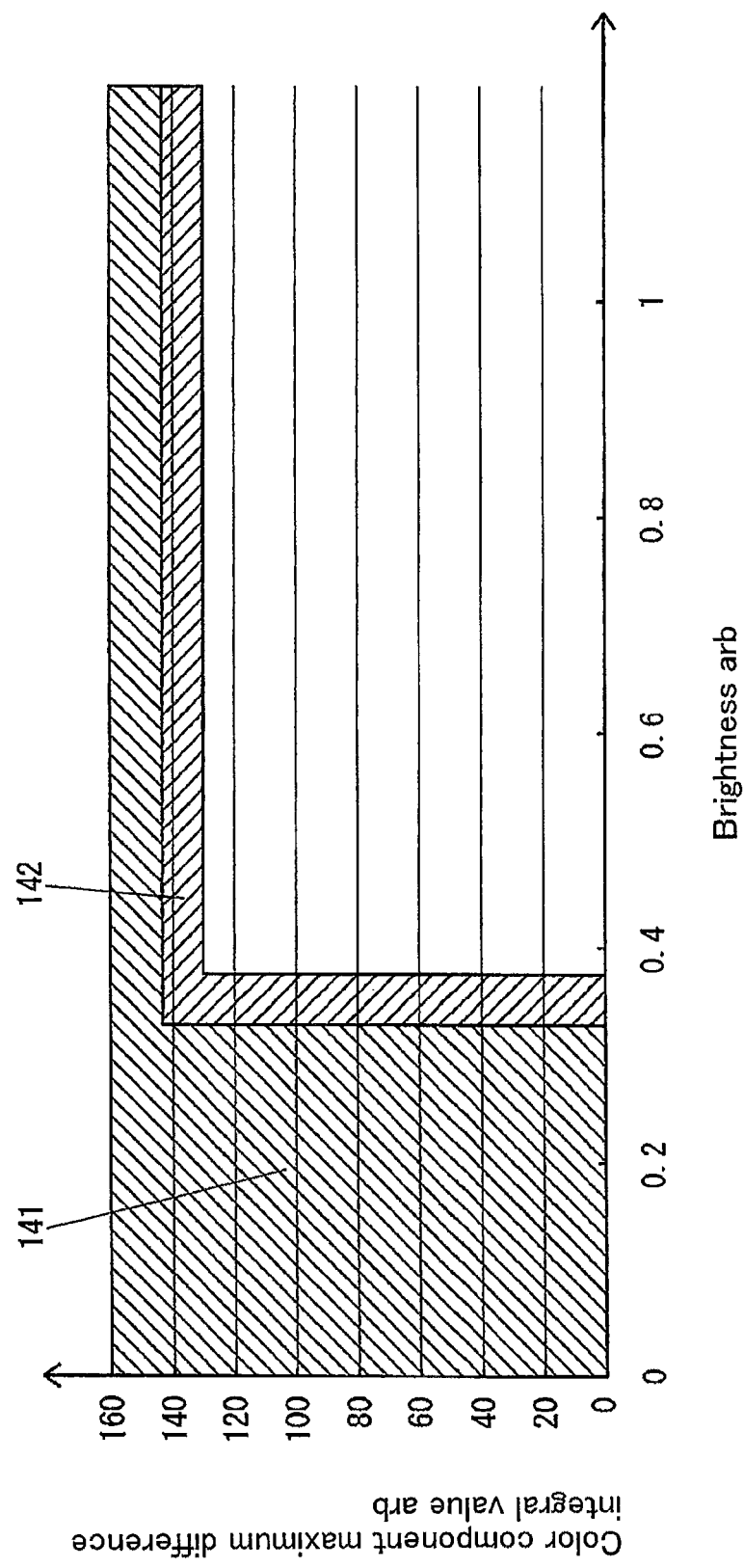
FIG. 17 is a diagram explaining an example of a threshold value used to determine the breakage state of a speed reducer shown in FIG. 6 when the color component calculation value is a color component maximum difference integral value.

FIG. 17 is a diagram explaining an example of a speed-reducer-breakage state determination threshold value 84c when the color component calculation value is a color component maximum difference integral value.

In FIG. 17, the unit of the ordinate axis is an arbitrary unit. The unit of the abscissa axis is an arbitrary unit in which the maximum value of brightness is defined as 1 whereas the minimum value thereof is defined as 0.

Based on the aforementioned experimental results, a person who determines the speed-reducer-breakage state determination threshold value 84c determines a range 141 of a combination in which the speed reducer 40 is presumed to have broken down and a range 142 of a combination in which the speed reducer 40 is presumed to require an overhaul and a repair although the speed reducer 40 has not broken down among possible combinations of the brightness and the color component maximum difference integral value of a color detected by the RGB sensor 73 of the oil state sensor 50 correspondingly to the deterioration of the lubricating oil 40a.

The speed-reducer-breakage state determination threshold value 84c is determined such that it is possible to determine whether the brightness and the color component maximum difference integral value of a color detected by the RGB sensor 73 of the oil state sensor 50 exist in the range 141 or in the range 142.

The aforementioned experimental results vary according to the type of the speed reducer 40 and the kind of the lubricating oil 40a. Therefore, the speed-reducer-breakage state determination threshold value 84c is determined depending on the type of the speed reducer 40 and the kind of the lubricating oil 40a.

The control portion 85 performs the operation of FIG. 13 under the condition that the color component calculation value is not a color component maximum difference but a color component maximum difference integral value.

More specifically, the color-component calculation value calculating means 85b calculates, as a color component calculation value, a color component maximum difference integral value, which is an integral value of the brightness of the difference between the maximum value and the minimum value among the R, G, and B values of a color detected by the RGB sensor 73 (S202).

Based on the lubricating-oil-deterioration state determination threshold value 84b, the state determining means 85c determines in which one of the ranges including the ranges 131 and 132 of FIG. 16 a combination of the brightness calculated in S201 and the color component maximum difference integral value calculated in S202 exists. In other words, the state determining means 85c determines that the deterioration state of the lubricating oil 40a is a state predetermined with respect to a combination of the brightness calculated in S201 and the color component maximum difference integral value calculated in S202 (S203).

When the state notifying means 85d does not determine in S205 that the lubricating oil 40a is abnormally deteriorated, the state determining means 85c determines, based on the speed-reducer-breakage state determination threshold value 84c, whether a combination of the brightness calculated in S201 and the color component maximum difference integral value calculated in S202 exists in the range 141 or in the range 142 of FIG. 17. In other words, the state determining means 85c determines that the breakage state of the speed reducer 40 is a state predetermined with respect to a combination of the brightness calculated in S201 and the color component maximum difference integral value calculated in S202 (S207).

An example in which the color component calculation value is a color component maximum ratio will be hereinafter described.

The color-component calculation value calculating means 85b is capable of calculating a color component maximum ratio as a color component calculation value according to an expression 3 shown below by using each of the R, G, and B values of a color detected by the RGB sensor 73.

$$\frac{\mathrm{MAX}(R, G, B)}{\mathrm{MIN}(R, G, B)} \qquad \text{[Expression 3]}$$

Figure 18:
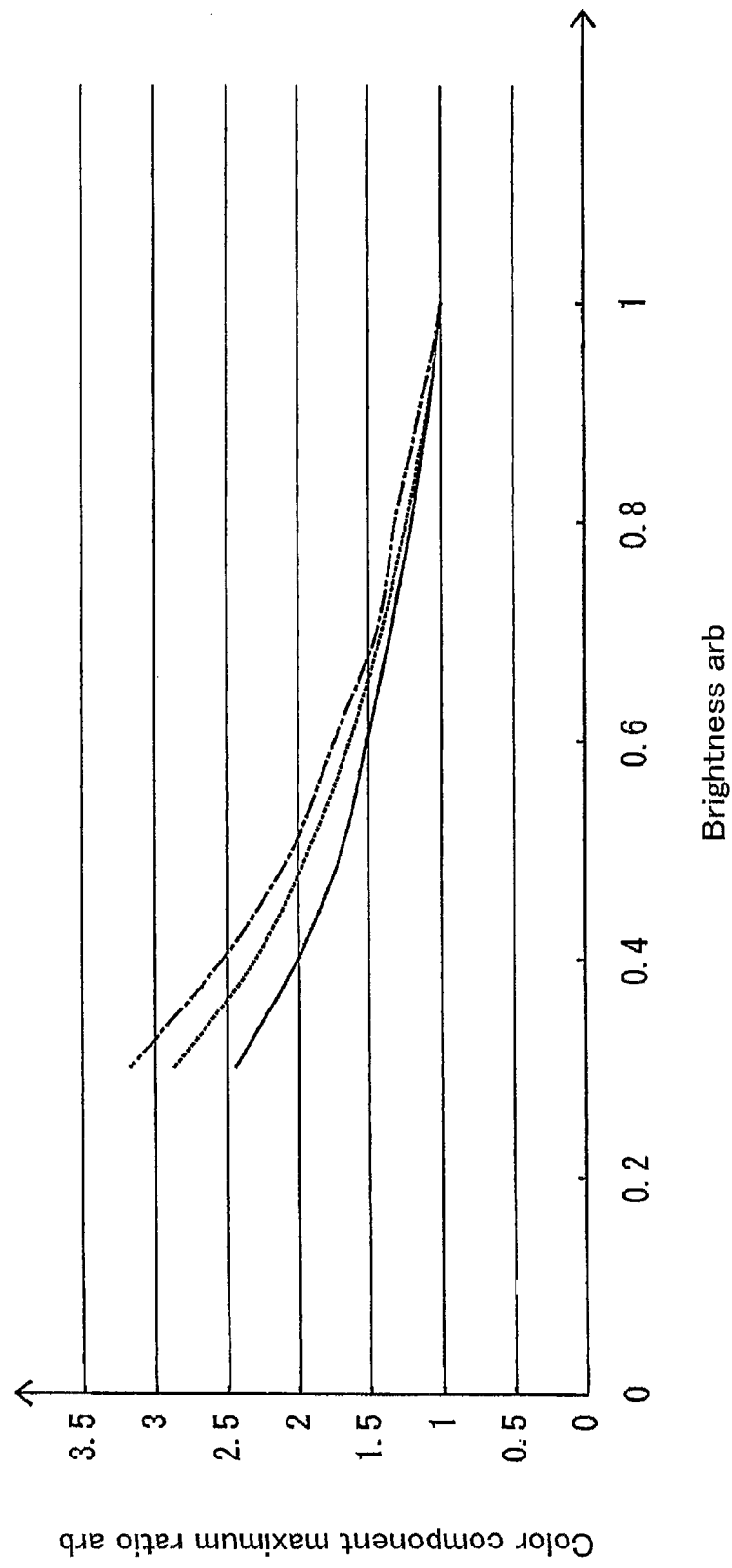
FIG. 18 is a graph showing an example of a relationship between brightness and a color component maximum ratio that are calculated by the computer of FIG. 2.

FIG. 18 is a graph showing an example of a relationship between brightness and a color component maximum ratio calculated by the computer 80.

In FIG. 18, the unit of the ordinate axis is an arbitrary unit. The unit of the abscissa axis is an arbitrary unit in which the maximum value of brightness is defined as 1 whereas the minimum value thereof is defined as 0.

Based on the output of the RGB sensor 73 of the oil state sensor 50, the shape of the graph showing a relationship between brightness and a color component maximum ratio calculated by the computer 80 is formed like those of three graphs shown in FIG. 18, for example.

FIG. 18 shows results of three experiments performed until the speed reducer 91 broke down. Each graph of FIG. 18 shows a result of each experiment. In fact, the number of times the experiment is performed is not limited to three, and the appropriateness of a lubricating-oil-deterioration state determination threshold value 84b and that of a speed-reducer-breakage state determination threshold value 84c become higher in proportion to an increase in the number of times the experiment is performed.

As shown in FIG. 18, when the experiment was started, each of the R, G, and B values of the color detected by the RGB sensor of the oil state sensor was a full-scale maximum value of output, and therefore the brightness was 1.0. When the experiment was started, the color component maximum ratio was 0.

According to the experimental results of FIG. 18, the brightness continued to decrease correspondingly to the deterioration of the lubricating oil until the speed reducer 91 broke down.

On the other hand, the color component maximum ratio continued to increase correspondingly to the deterioration of the lubricating oil until the speed reducer 91 broke down.

Next, a method for determining a lubricating-oil-deterioration state determination threshold value 84b will be described.

The inventors of the present invention have found out through the same experiment as the aforementioned experiment concerning the color component maximum difference that the deterioration state of the lubricating oil 40a of the speed reducer 40 has a strong correlation with the brightness and the color component maximum ratio of the color of light detected by the RGB sensor 73.

Figure 19:
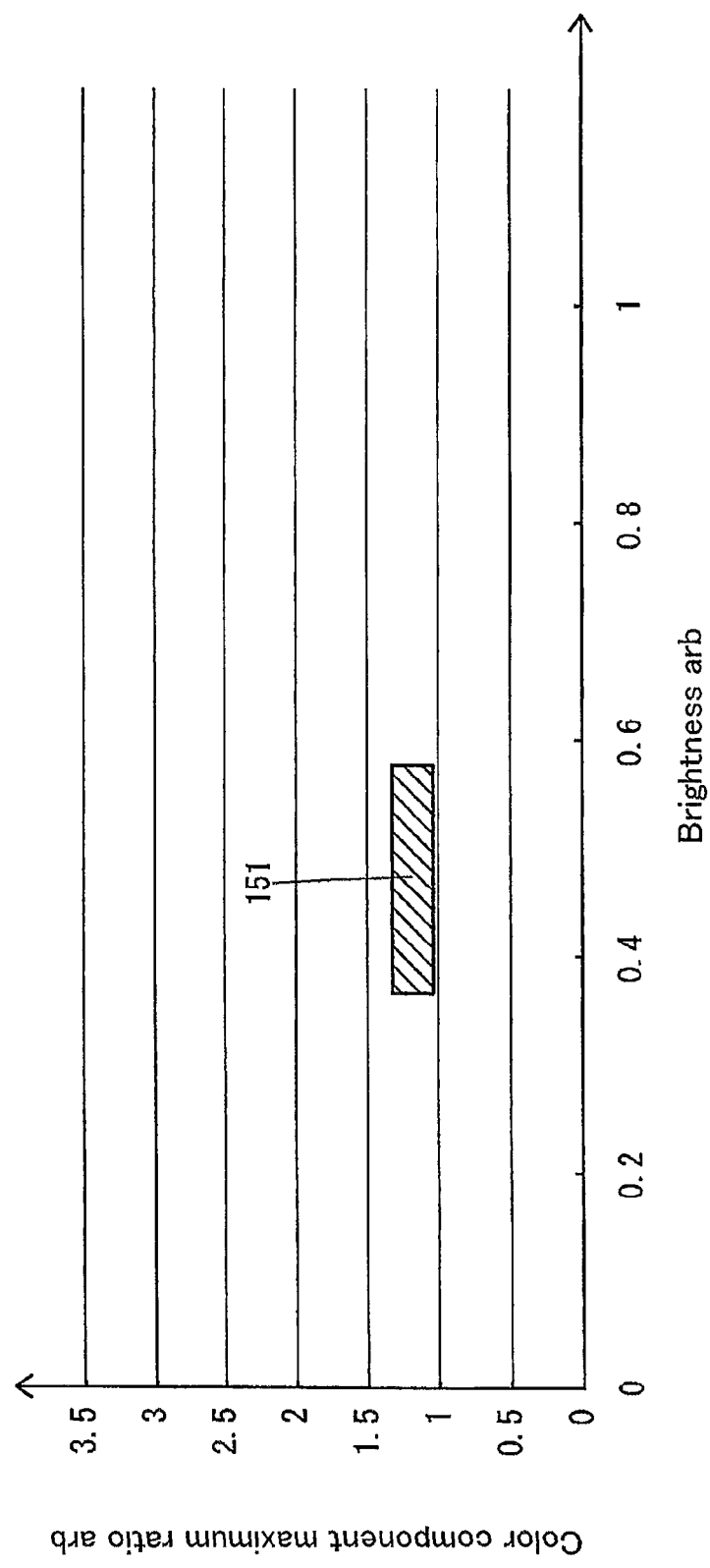
FIG. 19 is a diagram explaining an example of a threshold value used to determine the deterioration state of lubricating oil shown in FIG. 6 when the color component calculation value is a color component maximum ratio.

FIG. 19 is a diagram explaining an example of a lubricating-oil-deterioration state determination threshold value 84b when the color component calculation value is a color component maximum ratio.

In FIG. 19, the unit of the ordinate axis is an arbitrary unit. The unit of the abscissa axis is an arbitrary unit in which the maximum value of brightness is defined as 1 whereas the minimum value thereof is defined as 0.

Based on the aforementioned experimental results, a person who determines the lubricating-oil-deterioration state determination threshold value 84b divides, into a plurality of ranges, possible combinations of the brightness and the color component maximum ratio of a color detected by the RGB sensor 73 of the oil state sensor 50 correspondingly to the deterioration of the lubricating oil 40a. The range 151 is a range in which the lubricating oil 40a is presumed to be abnormally deteriorated by being mixed with impurities. Other ranges, such as a range in which the lubricating oil 40a is presumed to undergo no deterioration, a range in which the deterioration level of the lubricating oil 40a is presumed to be low, a range in which the deterioration level of the lubricating oil 40a is presumed to be intermediate, and a range in which the deterioration level of the lubricating oil 40a is presumed to be high, are also provided in the same way as in the example of FIG. 11 although these are not shown in FIG. 19.

The lubricating-oil-deterioration state determination threshold value 84b is determined such that it is possible to decide in which one of the ranges including the range 151 the brightness and the color component maximum ratio of the color detected by the RGB sensor 73 of the oil state sensor 50 exist.

The aforementioned experimental results vary according to the type of the speed reducer 40 and the kind of the lubricating oil 40a. Therefore, the lubricating-oil-deterioration state determination threshold value 84b is determined depending on the type of the speed reducer 40 and the kind of the lubricating oil 40a.

Next, a method for determining a speed-reducer-breakage state determination threshold value 84c will be described.

The inventors of the present invention have found out through the same experiment as the aforementioned experiment concerning the color component maximum difference that the breakage state of the speed reducer 40 has a strong correlation with the brightness and the color component maximum ratio of the color of light detected by the RGB sensor 73.

Figure 20:
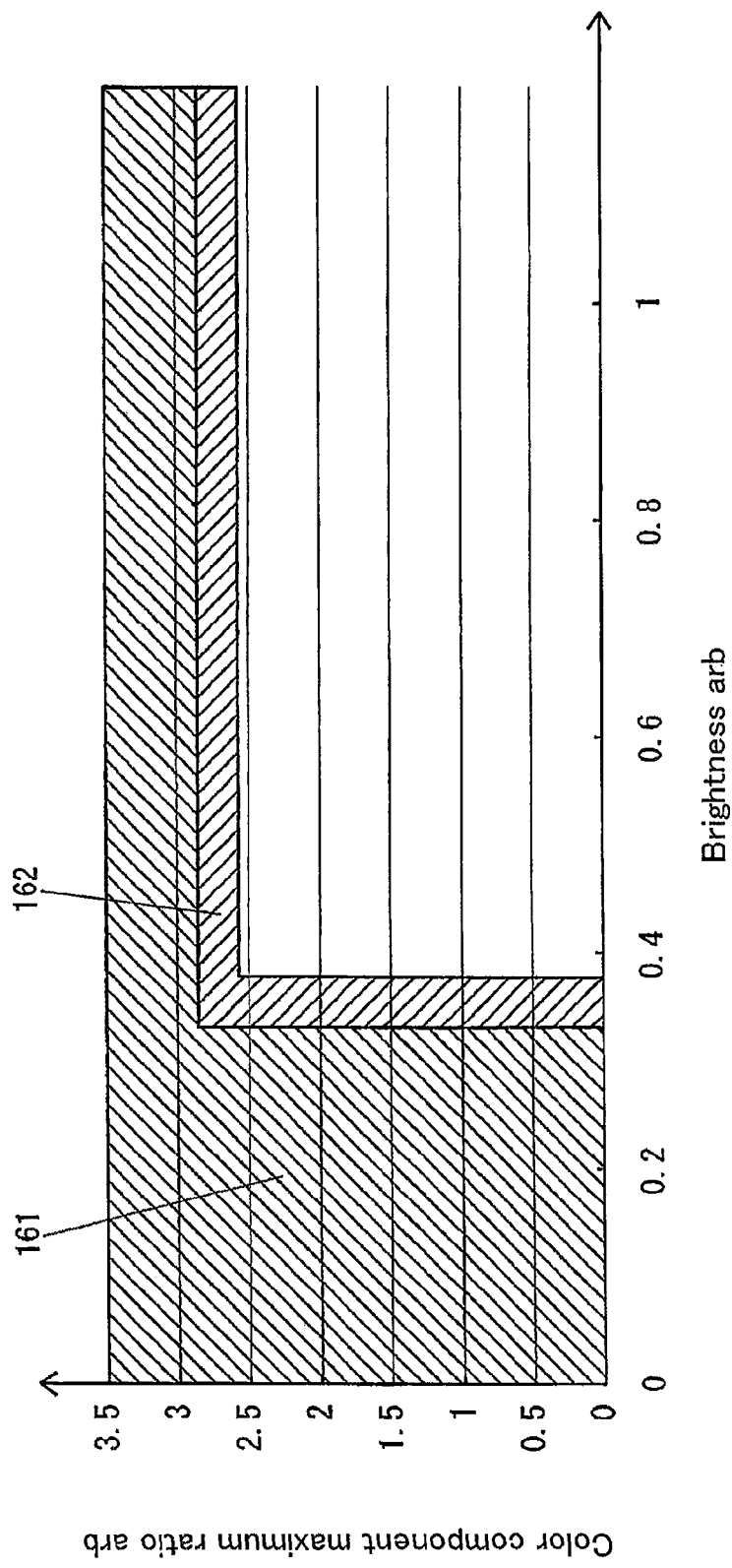
FIG. 20 is a diagram explaining an example of a threshold value used to determine the breakage state of a speed reducer shown in FIG. 6 when the color component calculation value is a color component maximum ratio.

FIG. 20 is a diagram explaining an example of a speed-reducer-breakage state determination threshold value 84c when the color component calculation value is a color component maximum ratio.

In FIG. 20, the unit of the ordinate axis is an arbitrary unit. The unit of the abscissa axis is an arbitrary unit in which the maximum value of brightness is defined as 1 whereas the minimum value thereof is defined as 0.

Based on the aforementioned experimental results, a person who determines the speed-reducer-breakage state determination threshold value 84c determines a range 161 of a combination in which the speed reducer 40 is presumed to have broken down and a range 162 of a combination in which the speed reducer 40 is presumed to require an overhaul and repair although the speed reducer 40 has not broken down among possible combinations of the brightness and the color component maximum ratio of a color detected by the RGB sensor 73 of the oil state sensor 50 correspondingly to the deterioration of the lubricating oil 40a.

The speed-reducer-breakage state determination threshold value 84c is determined such that it is possible to determine whether the brightness and the color component maximum ratio of a color detected by the RGB sensor 73 of the oil state sensor 50 exist in the range 161 or in the range 162.

The aforementioned experimental results vary according to the type of the speed reducer 40 and the kind of the lubricating oil 40a. Therefore, the speed-reducer-breakage state determination threshold value 84c is determined depending on the type of the speed reducer 40 and the kind of the lubricating oil 40a.

The control portion 85 performs the operation of FIG. 13 under the condition that the color component calculation value is not a color component maximum difference but a color component maximum ratio.

More specifically, the color-component calculation value calculating means 85b calculates, as a color component calculation value, a color component maximum ratio, which is the ratio between the maximum value and the minimum value among the R, G, and B values of a color detected by the RGB sensor 73 (S202).

Based on the lubricating-oil-deterioration state determination threshold value 84b, the state determining means 85c determines in which one of the ranges including the range 151 of FIG. 19 a combination of the brightness calculated in S201 and the color component maximum ratio calculated in S202 exists. In other words, the state determining means 85c determines that the deterioration state of the lubricating oil 40a is a state predetermined with respect to a combination of the brightness calculated in S201 and the color component maximum ratio calculated in S202 (S203).

When the state notifying means 85d does not determine in S205 that the lubricating oil 40a is abnormally deteriorated, the state determining means 85c determines, based on the speed-reducer-breakage state determination threshold value 84c, whether a combination of the brightness calculated in S201 and the color component maximum ratio calculated in S202 exists in the range 161 or in the range 162 of FIG. 20. In other words, the state determining means 85c determines that the breakage state of the speed reducer 40 is a state predetermined with respect to the combination of the brightness calculated in S201 and the color component maximum ratio calculated in S202 (S207).

An example in which the color component calculation value is a color component maximum ratio integral value will be hereinafter described.

The color-component calculation value calculating means 85b is capable of calculating, as a color component calculation value, a color component maximum ratio integral value, which is an integral value of the brightness of a color component maximum ratio by using each of the R, G, and B values of a color detected by the RGB sensor 73. More specifically, the color-component calculation value calculating means 85b is capable of calculating a color component maximum ratio integral value such that, each time brightness calculated by the brightness calculating means 85a while using each of the R, G, and B values of the color detected by the RGB sensor 73 changes, a color component maximum ratio that is a ratio between the maximum value and the minimum value among the R, G, and B values of the color detected by the RGB sensor 73 is added at that time.

Figure 21:
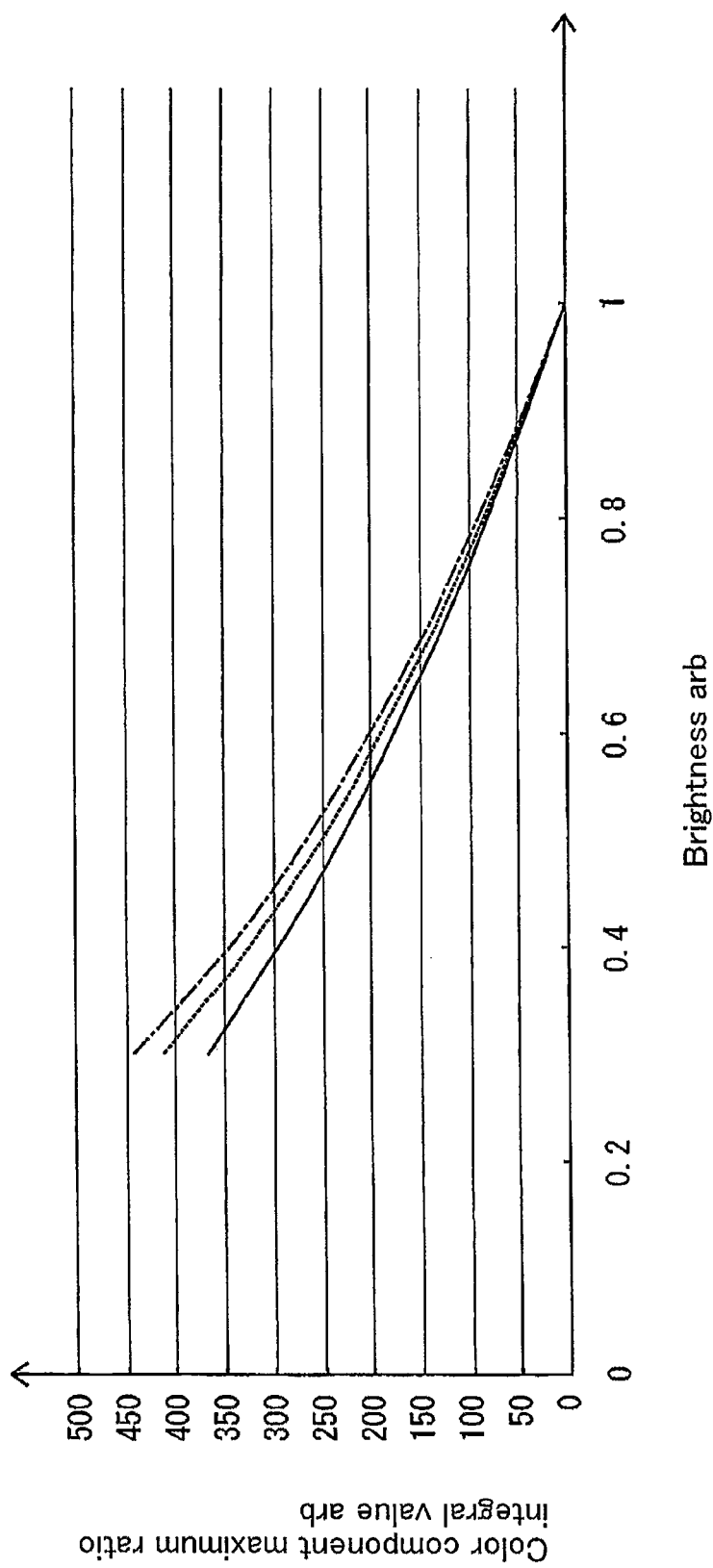
FIG. 21 is a graph showing an example of a relationship between brightness and a color component maximum ratio integral value that are calculated by the computer of FIG. 2.

FIG. 21 is a graph showing an example of a relationship between brightness and a color component maximum ratio integral value calculated by the computer 80.

In FIG. 21, the unit of the ordinate axis is an arbitrary unit. The unit of the abscissa axis is an arbitrary unit in which the maximum value of brightness is defined as 1 whereas the minimum value thereof is defined as 0.

Based on the output of the RGB sensor 73 of the oil state sensor 50, the shape of the graph showing a relationship between brightness and a color component maximum ratio integral value calculated by the computer 80 is formed like those of three graphs shown in FIG. 21, for example.

FIG. 21 shows results of three experiments performed until the speed reducer 91 broke down. Each graph of FIG. 21 shows a result of each experiment. In fact, the number of times the experiment is performed is not limited to three, and the appropriateness of a lubricating-oil-deterioration state determination threshold value 84b and that of a speed-reducer-breakage state determination threshold value 84c become higher in proportion to an increase in the number of times the experiment is performed.

As shown in FIG. 21, when the experiment was started, each of the R, G, and B values of the color detected by the RGB sensor of the oil state sensor was a full-scale maximum value of output, and therefore the brightness was 1.0. When the experiment was started, the color component maximum ratio integral value was 0.

According to the experimental results of FIG. 21, the brightness continued to decrease correspondingly to the deterioration of the lubricating oil until the speed reducer 91 broke down.

On the other hand, the color component maximum ratio integral value continued to increase correspondingly to the deterioration of the lubricating oil until the speed reducer 91 broke down.

Next, a method for determining a lubricating-oil-deterioration state determination threshold value 84b will be described.

The inventors of the present invention have found out through the same experiment as the aforementioned experiment concerning the color component maximum difference that the deterioration state of the lubricating oil 40a of the speed reducer 40 has a strong correlation with the brightness and the color component maximum ratio integral value of the color of light detected by the RGB sensor 73.

Figure 22:
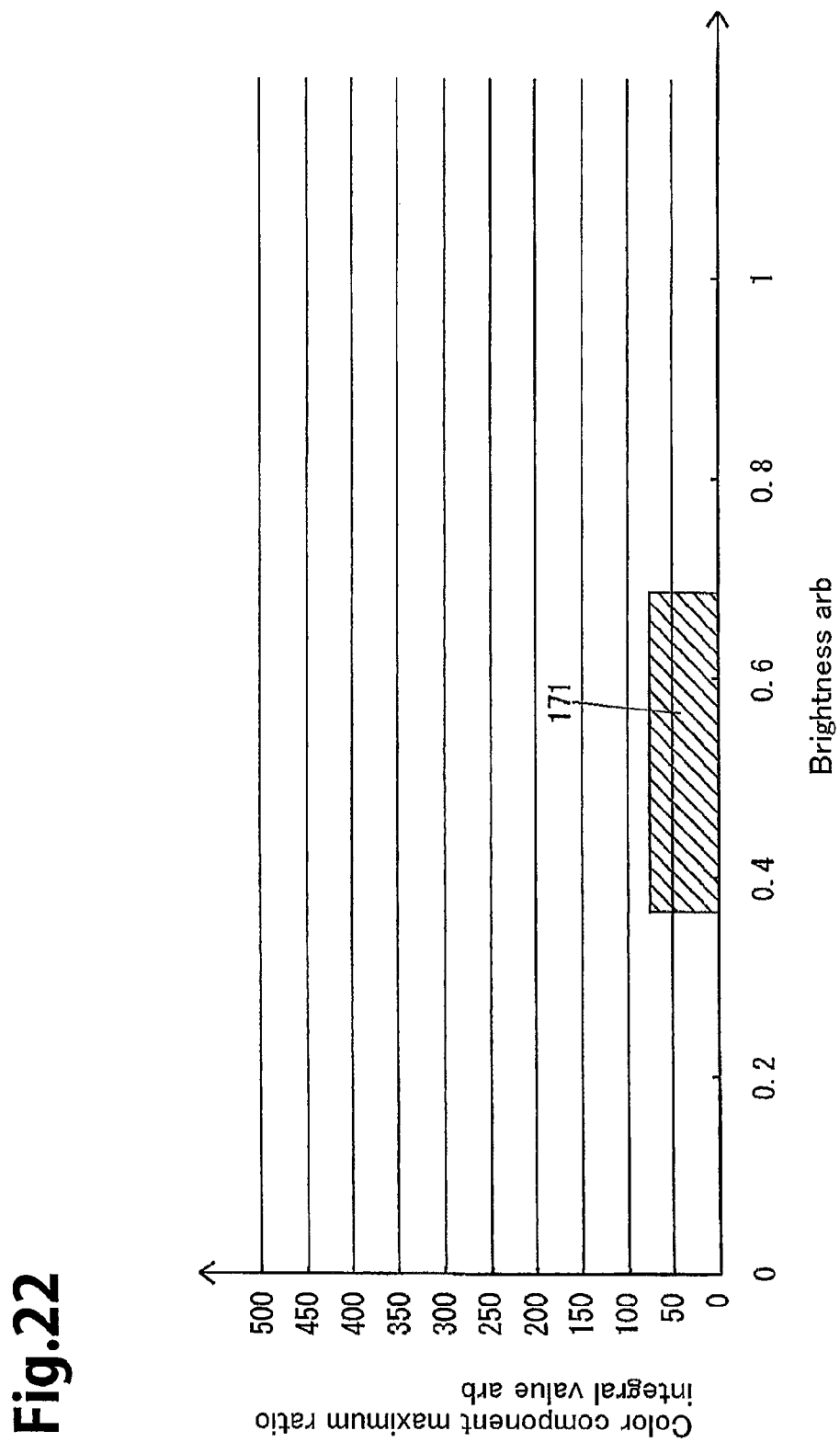
FIG. 22 is a diagram explaining an example of a threshold value used to determine the deterioration state of lubricating oil shown in FIG. 6 when the color component calculation value is a color component maximum ratio integral value.

FIG. 22 is a diagram explaining an example of a lubricating-oil-deterioration state determination threshold value 84b when the color component calculation value is a color component maximum ratio integral value.

In FIG. 22, the unit of the ordinate axis is an arbitrary unit. The unit of the abscissa axis is an arbitrary unit in which the maximum value of brightness is defined as 1 whereas the minimum value thereof is defined as 0.

Based on the aforementioned experimental results, a person who determines the lubricating-oil-deterioration state determination threshold value 84b divides, into a plurality of ranges, possible combinations of the brightness and the color component maximum ratio integral value of a color detected by the RGB sensor 73 of the oil state sensor 50 correspondingly to the deterioration of the lubricating oil 40a. The range 171 is a range in which the lubricating oil 40a is presumed to be abnormally deteriorated by being mixed with impurities. Other ranges, such as a range in which the lubricating oil 40a is presumed to undergo no deterioration, a range in which the deterioration level of the lubricating oil 40a is presumed to be low, a range in which the deterioration level of the lubricating oil 40a is presumed to be intermediate, and a range in which the deterioration level of the lubricating oil 40a is presumed to be high, are also provided in the same way as in the example of FIG. 11 although these are not shown in FIG. 22.

The lubricating-oil-deterioration state determination threshold value 84b is determined such that it is possible to decide in which of the ranges including the range 171 the brightness and the color component maximum ratio integral value of the color detected by the RGB sensor 73 of the oil state sensor 50 exist.

The aforementioned experimental results vary according to the type of the speed reducer 40 and the kind of the lubricating oil 40a. Therefore, the lubricating-oil-deterioration state determination threshold value 84b is determined depending on the type of the speed reducer 40 and the kind of the lubricating oil 40a.

Next, a method for determining a speed-reducer-breakage state determination threshold value 84c will be described.

The inventors of the present invention have found out through the same experiment as the aforementioned experiment concerning the color component maximum difference that the breakage state of the speed reducer 40 has a strong correlation with the brightness and the color component maximum ratio integral value of the color of light detected by the RGB sensor 73.

Figure 23:
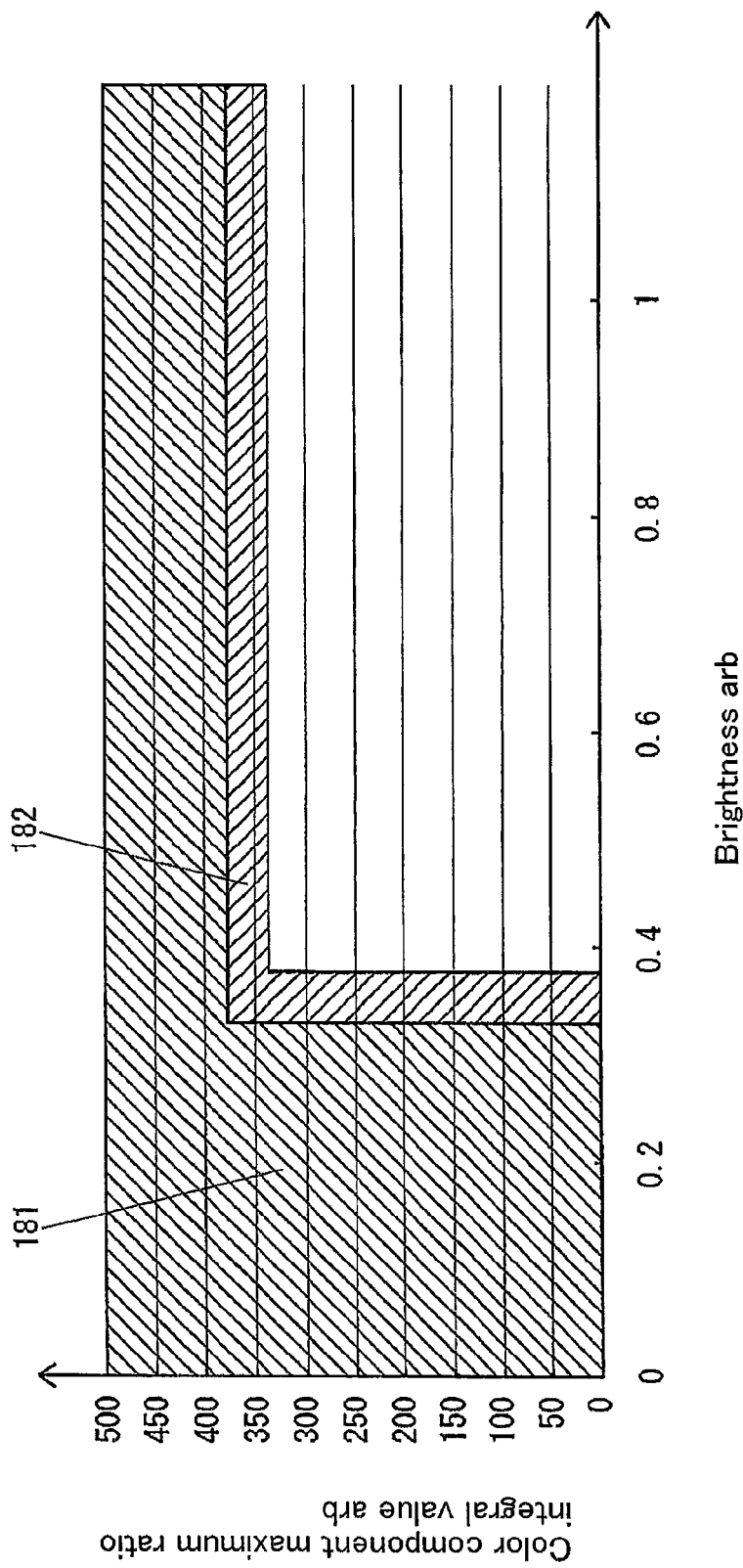
FIG. 23 is a diagram explaining an example of a threshold value used to determine the breakage state of a speed reducer shown in FIG. 6 when the color component calculation value is a color component maximum ratio integral value.

FIG. 23 is a diagram explaining an example of a speed-reducer-breakage state determination threshold value 84c when the color component calculation value is a color component maximum ratio integral value.

In FIG. 23, the unit of the ordinate axis is an arbitrary unit. The unit of the abscissa axis is an arbitrary unit in which the maximum value of brightness is defined as 1 whereas the minimum value thereof is defined as 0.

Based on the aforementioned experimental results, a person who determines the speed-reducer-breakage state determination threshold value 84c determines a range 181 of a combination in which the speed reducer 40 is presumed to have broken down and a range 182 of a combination in which the speed reducer 40 is presumed to require an overhauled and repair although the speed reducer 40 has not broken down among possible combinations of the brightness and the color component maximum ratio integral value of a color detected by the RGB sensor 73 of the oil state sensor 50 correspondingly to the deterioration of the lubricating oil 40a.

The speed-reducer-breakage state determination threshold value 84c is determined such that it is possible to determine whether the brightness and the color component maximum ratio integral value of a color detected by the RGB sensor 73 of the oil state sensor 50 exist in the range 181 or in the range 182.

The aforementioned experimental results vary according to the type of the speed reducer 40 and the kind of the lubricating oil 40a. Therefore, the speed-reducer-breakage state determination threshold value 84c is determined depending on the type of the speed reducer 40 and the kind of the lubricating oil 40a.

The control portion 85 performs the operation of FIG. 13 under the condition that the color component calculation value is not a color component maximum difference but a color component maximum ratio integral value.

More specifically, the color-component calculation value calculating means 85b calculates, as a color component calculation value, a color component maximum ratio integral value, which is an integral value of the brightness of the ratio between the maximum value and the minimum value among the R, G, and B values of a color detected by the RGB sensor 73 (S202).

Based on the lubricating-oil-deterioration state determination threshold value 84b, the state determining means 85c determines in which one of the ranges including the range 171 of FIG. 22 a combination of the brightness calculated in S201 and the color component maximum ratio integral value calculated in S202 exists. In other words, the state determining means 85c determines that the deterioration state of the lubricating oil 40a is a state predetermined with respect to a combination of the brightness calculated in S201 and the color component maximum ratio integral value calculated in S202 (S203).

When the state notifying means 85d does not determine in S205 that the lubricating oil 40a is abnormally deteriorated, the state determining means 85c determines, based on the speed-reducer-breakage state determination threshold value 84c, whether a combination of the brightness calculated in S201 and the color component maximum ratio integral value calculated in S202 exists in the range 181 or in the range 182 of FIG. 23. In other words, the state determining means 85c determines that the breakage state of the speed reducer 40 is a state predetermined with respect to a combination of the brightness calculated in S201 and the color component maximum ratio integral value calculated in S202 (S207).

Second Embodiment

First, a configuration to implement a state determining method according to this embodiment will be described.

The configuration to implement the state determining method according to the present embodiment is substantially the same as the configuration to implement the state determining method according to the first embodiment. In this second embodiment, the same reference numerals are given to components that are the same as those in the first embodiment, and detailed descriptions of this components are omitted. In the configuration to implement the state determining method according to the present embodiment, a description will be hereinafter given of parts that differ from the configuration to implement the state determining method according to the first embodiment.

Figure 24:
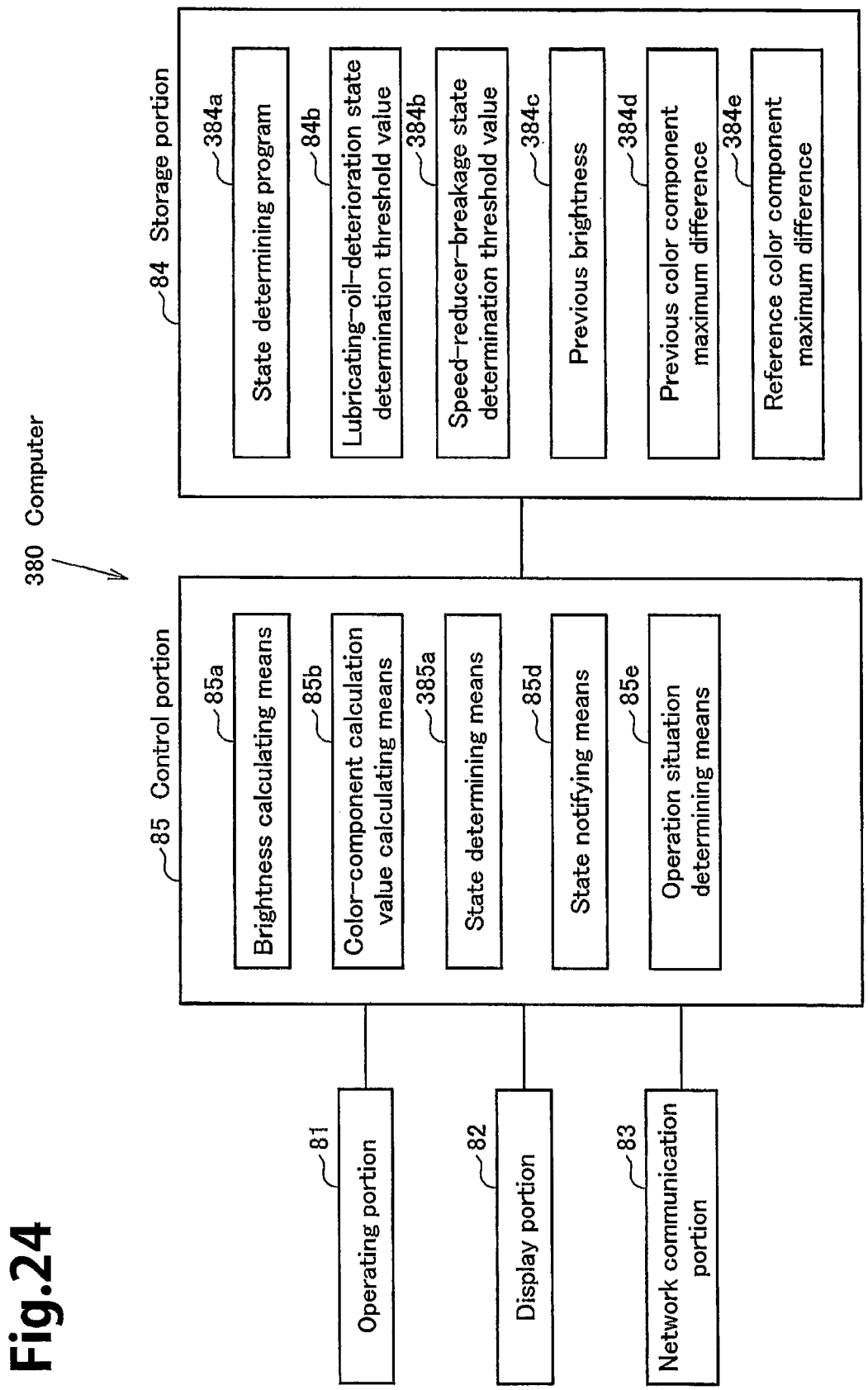
FIG. 24 is a block diagram of a computer of a state notification system that is one specific example of a configuration to implement a state determining method according to a second embodiment of the present invention.

A state notification system that is one specific example arranged to implement the state determining method according to the present embodiment is the same as in a configuration in which the state notification system 10 according to the first embodiment (see FIG. 2) has a computer 380 shown in FIG. 24 instead of the computer 80 (see FIG. 6).

FIG. 24 is a block diagram of the computer 380.

As shown in FIG. 24, the computer 380 is composed of a state determining program 384a that determines the deterioration state of the lubricating oil 40a of the speed reducer 40 of the industrial robot 20 and the breakage state of the speed reducer 40 of the industrial robot 20, a speed-reducer-breakage state determination threshold value 384b used to determine the breakage state of the speed reducer 40, and a state determining means 385a that determines a state based on brightness calculated by the brightness calculating means 85a and a color component maximum difference calculated by the color-component calculation value calculating means 85b, instead of the state determining program 84a(see FIG. 6), the speed-reducer-breakage state determination threshold value 84c (see FIG. 6), and the state determining means 85c (see FIG. 6) in comparison with the computer 80 (see FIG. 6).

The storage portion 84 of the computer 380 is capable of storing previous brightness 384c, which is brightness calculated last time, a previous color component maximum difference 384d, which is a color component maximum difference calculated last time, and a reference color component maximum difference 384e, which serves as a reference of the breakage state of the speed reducer 40. The storage portion 84 is capable of, for each of a plurality of oil state sensors 50 included in the industrial robot 20, storing the previous brightness 384c, the previous color component maximum difference 384d, and the reference color component maximum difference 384e.

The control portion 85 executes the state determining program 384a stored in the storage portion 84, and hence functions as the brightness calculating means 85a, functions as the color-component calculation value calculating means 85b, functions as the state determining means 385a, functions as the state notifying means 85d, and functions as the operation situation determining means 85e.

Next, a method for determining a speed-reducer-breakage state determination threshold value 384b will be described.

The inventors of the present invention have found out through an experiment performed according to the configuration of FIG. 7 that the breakage state of the speed reducer 40 has a strong correlation with the brightness and the color component maximum difference of the color of light detected by the RGB sensor 73.

Figure 25:
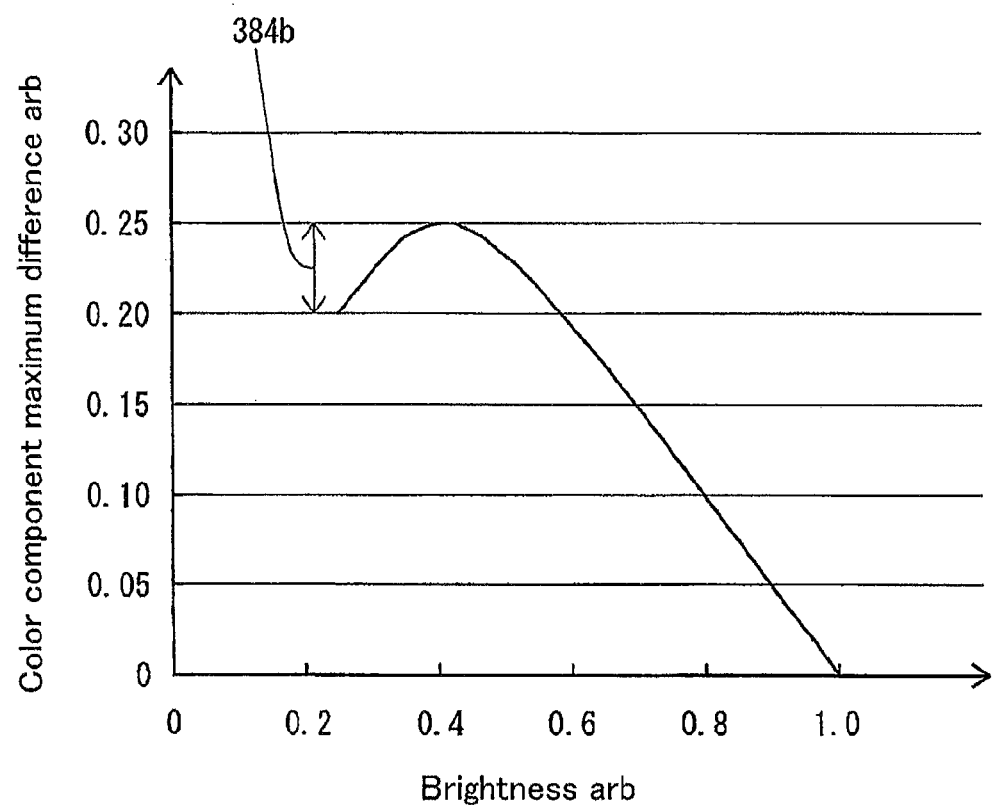
FIG. 25 is a diagram explaining an example of a threshold value used to determine the breakage state of a speed reducer shown in FIG. 24.

FIG. 25 is a diagram explaining an example of the speed-reducer-breakage state determination threshold value 384b.

In FIG. 25, the unit of the ordinate axis is an arbitrary unit in which the maximum value of the color component maximum difference is defined as 1 whereas the minimum value thereof is defined as 0. The unit of the abscissa axis is an arbitrary unit in which the maximum value of brightness is defined as 1 whereas the minimum value thereof is defined as 0.

Based on experimental results obtained according to the configuration of FIG. 7, a person who determines the speed-reducer-breakage state determination threshold value 384b determines the amount of decrease in the color component maximum difference as a speed-reducer-breakage state determination threshold value 384b after both the brightness and the color component maximum difference of a color detected by the RGB sensor 73 of the oil state sensor 50 correspondingly to the deterioration of the lubricating oil 40a start to decrease until the speed reducer 40 is presumed to have broken down as shown in FIG. 25. For example, the speed-reducer-breakage state determination threshold value 384b is "0.05."

Experimental results obtained according to the configuration of FIG. 7 vary according to the type of the speed reducer 40 and the kind of the lubricating oil 40a. Therefore, the speed-reducer-breakage state determination threshold value 384b is determined depending on the type of the speed reducer 40 and the kind of the lubricating oil 40a.

Next, a state determining method according to the present embodiment will be described.

Figure 26:
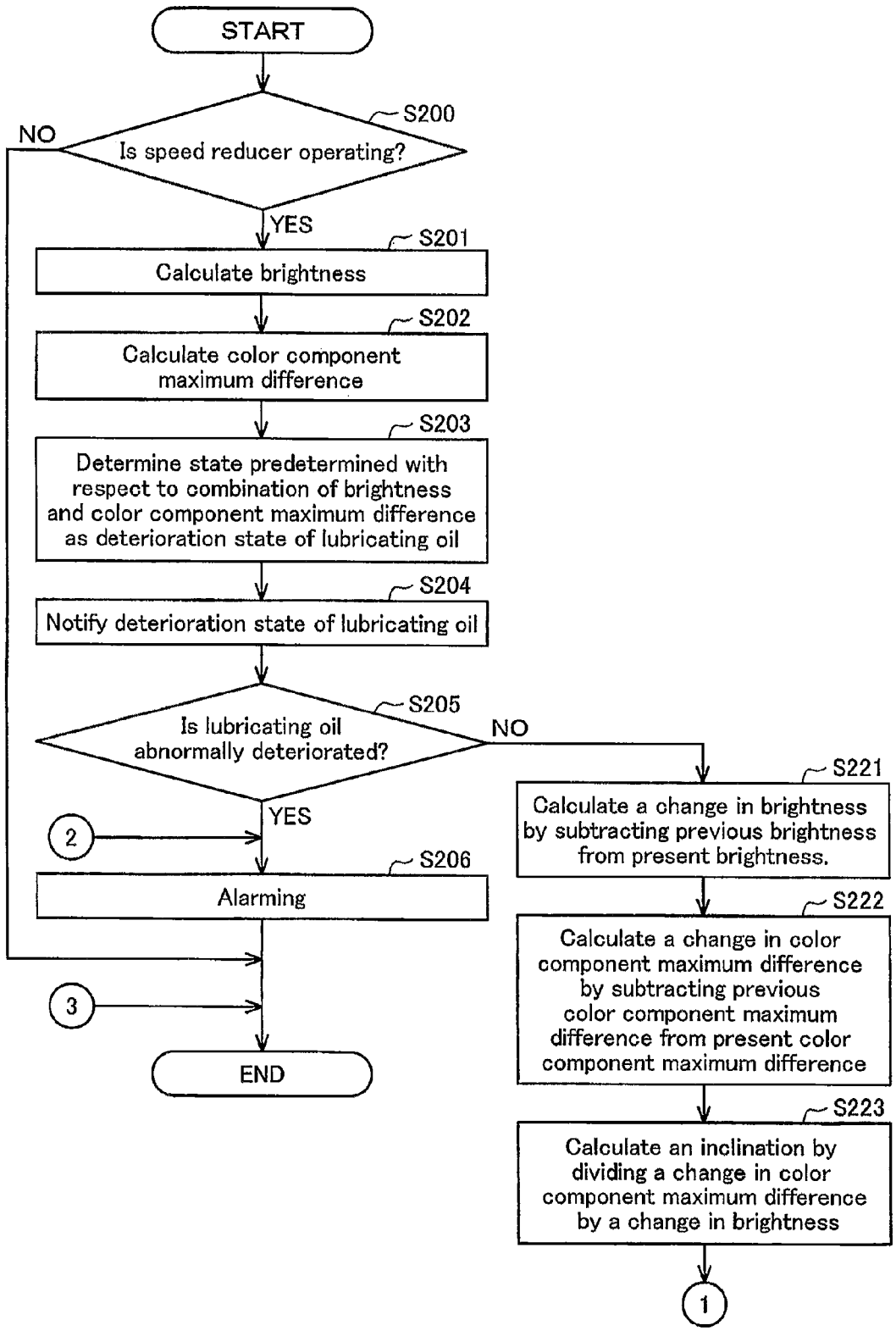
FIG. 26 is a flowchart of the operation of the computer of FIG. 24.

FIG. 26 is a flowchart of the operation of the computer 380. FIG. 27 is a flowchart of the operation subsequent to the operation of FIG. 26.

The computer 380 performs an operation shown in FIGS. 26 and 27 for each of a plurality of oil state sensors 50 included in the industrial robot 20. The operation of the computer 380 with respect to a single oil state sensor 50 will be hereinafter described.

In FIGS. 26 and 27, the same reference numerals are given to the same operations as in FIG. 13, and detailed descriptions of the same operations are omitted.

The computer 380 executes the state determining program 384a, and hence performs the operation of FIG. 26 and of FIG. 27 at predetermined time intervals for each oil state sensor 50. It is possible for a user of the computer 380 to set the time intervals arbitrarily, e.g., at time intervals of six hours.

As shown in FIGS. 26 and 27, the computer 380 performs the same operation as in S200 to S206 shown in FIG. 13.

When the state notifying means 85*d* does not determine in S205 that the lubricating oil 40*a* is abnormally deteriorated, the state determining means 385*a* calculates a change in brightness by subtracting the previous brightness 384*c* stored in S232 (described below) of the previous operation shown in FIGS. 26 and 27 from the present brightness calculated in S201 (S221). The state determining means 385*a* calculates the change in brightness as 0 when the previous brightness 384*c* is not stored.

Thereafter, the state determining means 385*a* calculates a change in color component maximum difference by subtracting the previous color component maximum difference 384*d* stored in S233 (described below) of the previous operation shown in FIGS. 26 and 27 from the present color component maximum difference calculated in S202 (S222). The state determining means 385*a* calculates the change in color component maximum difference as 0 when the previous color component maximum difference 384*d* is not stored.

Thereafter, the state determining means 385*a* calculates an inclination by dividing the change in color component maximum difference calculated in S222 by the change in brightness calculated in S221 (S223). If the change in brightness calculated in S221 is 0, the state determining means 385*a* calculates that the inclination has a negative value when the change in color component maximum difference calculated in S222 has a positive value, and that the inclination is zero when the change in color component maximum difference calculated in S222 is zero, and that the inclination has a positive value when the change in color component maximum difference calculated in S222 has a negative value.

Thereafter, the state determining means 385*a* determines whether the inclination calculated in S223 is a positive value or not (S224).

When it is determined in S223 that the inclination calculated in S224 is not a positive value, the state determining means 385*a* determines that the speed reducer 40 has not broken down (S225).

On the other hand, when it is determined in S223 that the inclination calculated in S224 is a positive value, the state determining means 385*a* determines whether the reference color component maximum difference 384*e* is stored or not (S226).

When it is determined in S226 that the reference color component maximum difference 384*e* is not stored, the state determining means 385*a* causes the storage portion 84 to store the present color component maximum difference calculated in S202 as a reference color component maximum difference 384*e* (S227).

When it is determined in S226 that the reference color component maximum difference 384*e* is stored or when the step S227 is ended, the state determining means 385*a* calculates the amount of decrease in the color component maximum difference from the reference color component maximum difference 384*e* by subtracting the present color component maximum difference calculated in S202 from the reference color component maximum difference 384*e* (S228).

Thereafter, the state determining means 385*a* determines whether the amount of decrease calculated in S228 is greater than the speed-reducer-breakage state determination threshold value 384*b* (S229).

When it is determined in S229 that the amount of decrease calculated in S228 is less than the speed-reducer-breakage state determination threshold value 384*b*, the state determining means 385*a* determines time until the speed reducer 40 breaks down based on time intervals at which the operation shown in FIGS. 26 and 27 is performed, the speed-reducer-breakage state determination threshold value 384*b*, the change in the color component maximum difference calculated in S222, and the amount of decrease calculated in S228 (S230). In other words, the state determining means 385*a* calculates the amount of decrease in the color component maximum difference from the present time until the speed reducer 40 breaks down by subtracting the amount of decrease calculated in S228 from the speed-reducer-breakage state determination threshold value 384*b*, thereafter calculates the number of remaining times the operation shown in FIGS. 26 and 27 is performed from the present time until the speed reducer 40 breaks down by dividing this amount of decrease by a change in the color component maximum difference calculated in S222, and calculates time until the speed reducer 40 breaks down from the present time by multiplying this number of remaining times of the performance by the time intervals at which the operation shown in FIGS. 26 and 27 is performed.

For example, suppose that the time intervals at which the operation shown in FIGS. 26 and 27 is performed are time intervals of six hours, the speed-reducer-breakage state determination threshold value 384*b* is 0.05, the change in the color component maximum difference calculated in S222 is 0.005, and the amount of decrease calculated in S228 is 0.03. In this case, the state determining means 385*a* calculates 0.02, which is the amount of decrease in the color component maximum difference until the speed reducer 40 breaks down from the present time, by subtracting 0.03, which is the amount of decrease calculated in S228, from 0.05, which is the speed-reducer-breakage state determination threshold value 384*b*. The state determining means 385*a* also calculates 4, which is the number of remaining times the operation shown in FIGS. 26 and 27 is performed until the speed reducer 40 breaks down from the present time, by dividing the resulting amount of decrease by 0.005, which is the change in the color component maximum difference calculated in S222, and calculates 24 hours, which is time until the speed reducer 40 breaks down from the present time, by multiplying the resulting number of remaining times of the performance by six hours, which is the time of the time intervals at which the operation shown in FIGS. 26 and 27 is performed.

When it is determined in S229 that the amount of decrease calculated in S228 is equal to or is greater than the speed-reducer-breakage state determination threshold value 384*b*, the state determining means 385*a* determines that the speed reducer 40 has broken down (S231).

When the step S225 or the step S230 is ended, the state determining means 385*a* causes the storage portion 84 to store the present brightness calculated in S201 as the previous brightness 384*c* (S232). If the storage portion 84 has already stored the previous brightness 384*c*, the state determining means 385*a* overwrites the present brightness calculated in S201 as new previous brightness 384*c*.

Thereafter, the state determining means 385*a* causes the storage portion 84 to store the present color component maximum difference calculated in S202 as the previous color component maximum difference 384*d* (S233). If the storage portion 84 has already stored the previous color component maximum difference 384*d*, the state determining means 385*a* overwrites the present color component maximum difference calculated in S202 as a new previous color component maximum difference 384*d*.

When the state determining means 385*a* ends the step S231 or the step S233, the state notifying means 85*d* notifies the breakage state of the speed reducer 40 determined in S225, S230, or S231 as "State of Speed Reducer" to the display portion 82 as shown in, for example, FIG. 28 (S208).

FIG. 28 is a diagram showing an example of the display of the display portion 82.

In FIG. 28, the state of the speed reducer A is displayed as "Normal," and the state of the speed reducer B is displayed as "24 hours to Breakdown," and the state of the speed reducer C is displayed as "Breakdown."

As shown in FIGS. 26 and 27, the state notifying means 85d determines whether alarming is necessary after the step S208 is completed (S209). If time until the breakdown of the speed reducer 40 determined in S230 is, for example, one week or less or if it is determined in S231 that the speed reducer 40 has broken down, the state notifying means 85d determines that alarming is necessary.

When it is determined in S209 that alarming is necessary, the state notifying means 85d performs alarming, for example, by inverting colors on the display of the display portion 82 (S206).

In the display of FIG. 28, alarming is performed by inverting colors of the state of the speed reducer B and the state of the speed reducer C. Therefore, it is possible for a user of the computer 380 to easily recognize that the speed reducer B has 24 hours until breakdown and requires an overhaul and repair or that the speed reducer C has broken down.

As shown in FIGS. 26 and 27, when it is determined in S200 that the speed reducer 40 is not operating or when the step S206 ends or when it is determined in S209 that alarming is not necessary, the control portion 85 completes the operation of FIG. 26 and of FIG. 27.

When the lubricating oil 40a is changed or the speed reducer 40 is replaced, a user of the computer 380 commands the computer 380 through the operating portion 81 to delete the previous brightness 384c that corresponds to the lubricating oil 40a that has been changed or the speed reducer 40 that has been replaced, to delete the previous color component maximum difference 384d, and to delete the reference color component maximum difference 384e from the storage portion 84. Therefore, the control portion 85 of the computer 380 deletes the previous brightness 384c, the previous color component maximum difference 384d, and the reference color component maximum difference 384e from the storage portion 84 in response to the command issued by the user.

When the lubricating oil 40a is changed, the brightness calculated by the brightness calculating means 85a becomes greatly higher after changing the lubricating oil 40a than before changing the lubricating oil 40a. Therefore, based on a change in brightness calculated by the brightness calculating means 85a, the control portion 85 of the computer 380 is capable of automatically determining that the lubricating oil 40a has been changed. Although brightness has been described above, each of the R, G, and B values of a color detected by the RGB sensor 73 also becomes greatly higher after changing the lubricating oil 40a than before changing the lubricating oil 40a when the lubricating oil 40a is changed. Therefore, based on a change in any one of the R, G, and B values of the color detected by the RGB sensor 73, the control portion 85 of the computer 380 is capable of automatically determining that the lubricating oil 40a has been changed. If a configuration is formed to automatically determine that the lubricating oil 40a has been changed, the control portion 85 of the computer 380 is also capable of automatically deleting the previous brightness 384c, the previous color component maximum difference 384d, and the reference color component maximum difference 384e from the storage portion 84 when it is determined that the lubricating oil 40a has been changed.

As described above, the state determining method according to the present embodiment determines the breakage state of the speed reducer 40 (S229) in accordance with the amount of decrease in the color component maximum difference, i.e., in accordance with the amount of decrease calculated in S228 in comparison with that at a point of time when both the brightness calculated in S201 and the color component maximum difference calculated in S202 start to decrease (YES in S224). In other words, not based on a simple combination of the brightness and the color component maximum difference of the color of light detected by the RGB sensor 73 as in the state determining method according to the first embodiment, but based on a change in the brightness and the color component maximum difference of the color of light detected by the RGB sensor 73, the state determining method according to the present embodiment determines the breakage state of the speed reducer 40. Therefore, the state determining method according to the present embodiment is capable of reducing the influence of the individual differences of the speed reducer 40 and the influence of the individual differences of the lubricating oil 40a on the determination of the breakage state of the speed reducer 40, and therefore it is possible to raise the accuracy of the determination of the breakage state of the speed reducer 40.

When both the brightness calculated in S201 and the color component maximum difference calculated in S202 decrease (YES in S224), the state determining method according to the present embodiment determines time until breakdown of the speed reducer 40 as the breakage state of the speed reducer 40 in accordance with time intervals at which the operation shown in FIGS. 26 and 27 is performed and in accordance with the amount of decrease in the color component maximum difference at the time intervals, i.e., in accordance with a change in the color component maximum difference calculated in S222 (S230). Therefore, the state determining method according to the present embodiment determines time until breakdown of the speed reducer 40, and therefore it is possible to improve the convenience of a user of the speed reducer 40.

Although the arithmetic processing portion 5 of FIG. 1 is realized by the control portion 85 of the computer 80 or the computer 380 in each embodiment mentioned above, it may be realized by being arranged exclusive of the control portion of the computer. For example, the arithmetic processing portion 5 of FIG. 1 may be realized by an electronic component in the electronic component group 70 of the oil state sensor 50. In this example, it is only necessary for this electronic component to store various pieces of data, such as the lubricating-oil-deterioration state determination threshold value 84b, and to perform the operation of FIG. 13 or the operation of FIGS. 26 and 27, and to cause the external display device 6, such as a PC display portion, to display a determination result.

Additionally, although the machine of the present invention is a speed reducer used for industrial robots in each embodiment mentioned above, the present invention may be applied to machines other than the speed reducer for the industrial robot. For example, when an air compressor that generates compressed air for use in railway vehicles is employed as a machine of the present invention, the oil of the present invention may be lubricating-oil of this air compressor. When a traveling motor for architectural machines or a valve for architectural machines is employed as a machine of the present invention, the oil of the present invention may be lubricating oil of this traveling motor or hydraulic oil of this valve. When a windmill is employed as a machine of the present invention, the oil of the present invention may be lubricating oil of this windmill. When a conveyance engine, such as a vessel engine, is employed as a machine of the present invention, the oil of the present invention may be engine oil of this engine. When a flight control actuator that controls the flight posture of an aircraft is employed as a machine of the present invention, the oil of the present invention may be hydraulic oil of this flight control actuator. When a machine tool is employed as a machine of the present invention, the oil of the present invention may be cutting-oil of this machine tool. When a vacuum pump is employed as a machine of the present invention, the oil of the present invention may be lubricating oil of this vacuum pump.

DESCRIPTION OF THE REFERENCE NUMERALS

1 Light-emitting element
1a Light
2 Light-receiving element
6 Display device
9 Oil
10 State notification system
40 Speed reducer (Machine)
40a Lubricating oil (Oil)
60 Gap-forming member
60a Oil receiving gap
72 White LED (Light-emitting element)
72a Optical path
73 RGB sensor (Light-receiving element)
80 Computer
82 Display portion
84a State determining program
85a Brightness calculating means
85b Color-component calculation value calculating means
85c State determining means
380 Computer
384a State determining program
385a State determining means

The invention claimed is:

1. A state determining method for determining at least either one of a deterioration state of oil of a machine and a breakage state of the machine, the state determining method comprising:
a light emission step of causing white light emitted by a light-emitting element to pass through the oil;
a light receiving step of causing a light-receiving element to detect a color of the light that has passed through the oil according to the light emission step;
a brightness calculation step of calculating brightness of the color detected according to the light receiving step;
a color component calculation value calculating step of calculating a color component calculation value that is a value calculated based on a maximum value and a minimum value among an R value, a G value, and a B value of the color detected according to the light receiving step; and
a state determination step of determining the state based on the brightness calculated according to the brightness calculation step and the color component calculation value calculated according to the color component calculation value calculating step,
wherein the color component calculation value is a difference between the maximum value and the minimum value,
wherein the state determination step includes a machine breakage state determining step of determining the breakage state of the machine in accordance with an amount of decrease in the color component calculation value in comparison with that at a point of time when both the brightness calculated according to the brightness calculation step and the color component calculation value calculated according to the color component calculation value calculating step start to decrease, and
wherein when both the brightness calculated according to the brightness calculation step and the color component calculation value calculated according to the color component calculation value calculating step decrease, the machine breakage state determining step is a step of determining time until the machine breaks down as the breakage state of the machine in accordance with time intervals at which the machine breakage state determining step is performed and in accordance with an amount of decrease in the color component calculation value at the time intervals.

2. The state determining method according to claim 1, wherein
the state determination step includes an oil deterioration state determining step of determining the deterioration state of the oil, and
the oil deterioration state determining step is a step of determining that the deterioration state of the oil is a state predetermined with respect to a combination of the brightness calculated according to the brightness calculation step and the color component calculation value calculated according to the color component calculation value calculating step.

3. The state determining method according to claim 1, wherein the machine breakage state determining step is a step of determining that the breakage state of the machine is a state predetermined with respect to a combination of the brightness calculated according to the brightness calculation step and the color component calculation value calculated according to the color component calculation value calculating step.

4. The state determining method according to claim 1, further comprising a received-light output adjusting step of adjusting an output of the light-receiving element,
wherein the received-light output adjusting step is a step of turning the color of the output of the light-receiving element black when an arrival of the light at the light-receiving element is intercepted and of turning the color of the output of the light-receiving element white when the oil is introduced into the machine.

5. The state determining method according to claim 1, wherein
the color component calculation value is a difference between the maximum value and the minimum value, and
the color component calculation value calculating step is a step of calculating a difference between the R value and the B value of the color detected according to the light receiving step as the color component calculation value.

6. A state notification system for notifying at least either one of a deterioration state of oil of a machine and a breakage state of the machine, the state notification system comprising:
a light-emitting element that emits white light;
a light-receiving element that detects a color of received light;
a gap-forming member in which a gap for oil into which the oil enters is located on an optical path from the light-emitting element to the light-receiving element;
a brightness calculating means for calculating brightness of the color detected by the light-receiving element;
a color-component calculation value calculating means for calculating a color component calculation value that is a value calculated based on a maximum value and a minimum value among an R value, a G value, and a B value of the color detected by the light-receiving element;

a state determining means for determining the state based on the brightness calculated by the brightness calculating means and the color component calculation value calculated by the color-component calculation value calculating means; and a display device that notifies the state determined by the state determining means, wherein the color component calculation value is a difference between the maximum value and the minimum value, wherein the state determining means includes a machine breakage state determining means for determining the breakage state of the machine in accordance with an amount of decrease in the color component calculation value in comparison with that at a point of time when both the calculated brightness and the calculated color component calculation value start to decrease, and wherein when both the calculated brightness and the calculated color component calculation value decrease, the machine breakage state determining means determines time until the machine breaks down as the breakage state of the machine in accordance with time intervals at which the breakage state of the machine is determined and in accordance with an amount of decrease in the color component calculation value at the time intervals.

7. A non-transitory computer-readable storage medium with an executable program stored thereon, the program causing a computer to perform:

a brightness calculation step of calculating brightness of a color of light detected by a light-receiving element at which white light that has been emitted by a light-emitting element and passed through the oil and arrives;

a color component calculation value calculating step of calculating a color component calculation value that is a value calculated based on a maximum value and a minimum value among an R value, a G value, and a B value of the color detected by the light-receiving element; and a state determination step of determining the state based on the brightness calculated according to the brightness calculation step and the color component calculation value calculated according to the color component calculation value calculating step, wherein the color component calculation value is a difference between the maximum value and the minimum value, wherein the state determination step includes a machine breakage state determining step of determining the breakage state of the machine in accordance with an amount of decrease in the color component calculation value in comparison with that at a point of time when both the brightness calculated according to the brightness calculation step and the color component calculation value calculated according to the color component calculation value calculating step start to decrease, and wherein when both the brightness calculated according to the brightness calculation step and the color component calculation value calculated according to the color component calculation value calculating step decrease, the machine breakage state determining step is a step of determining time until the machine breaks down as the breakage state of the machine in accordance with time intervals at which the machine breakage state determining step is performed and in accordance with an amount of decrease in the color component calculation value at the time intervals.

\* \* \* \* \*